(12) United States Patent
Olsson et al.

(10) Patent No.: US 8,470,872 B2
(45) Date of Patent: Jun. 25, 2013

(54) COMPOUNDS WITH ACTIVITY AT ESTROGEN RECEPTORS

(75) Inventors: Roger Olsson, Bunkeflostrand (SE); Lene Hyldtoft, Lyndby (DK); Magnus Gustafsson, Frederiksberg (SE); Brigitte Winther Lund, Bagsvaerd (DK)

(73) Assignee: Acadia Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 13/325,160

(22) Filed: Dec. 14, 2011

(65) Prior Publication Data

US 2012/0088825 A1 Apr. 12, 2012

Related U.S. Application Data

(62) Division of application No. 12/258,313, filed on Oct. 24, 2008, now Pat. No. 8,101,651.

(60) Provisional application No. 60/983,078, filed on Oct. 26, 2007.

(51) Int. Cl.
*A61K 31/381* (2006.01)

(52) U.S. Cl.
USPC .......................................................... 514/443

(58) Field of Classification Search
USPC .......................................................... 514/443
See application file for complete search history.

(56) References Cited

U.S. PATENT DOCUMENTS

| 8,101,651 B2 | 1/2012 | Olsson et al. |
| 2006/0004087 A1 | 1/2006 | Miller et al. |
| 2009/0131510 A1 | 5/2009 | Olsson et al. |

FOREIGN PATENT DOCUMENTS

| CN | 101835770 A | | 9/2010 |
| EP | 2200994 A1 | | 6/2010 |
| WO | 0037065 A2 | | 6/2000 |
| WO | 2005108337 A2 | | 11/2005 |
| WO | WO 2005/108337 | * | 11/2005 |
| WO | 2007038636 A2 | | 4/2007 |
| WO | 2007056500 A2 | | 5/2007 |
| WO | 2008033894 A2 | | 3/2008 |
| WO | 2009055734 A1 | | 4/2009 |

OTHER PUBLICATIONS

International Search Report and Written Opinion dated Jan. 27, 2009 issued in PCT/US2008/081211.
Preliminary Report on Patentability dated May 6, 2010 issued in PCT/US2008/081211.
Behl, Estrogen can protect neurons: modes of action. J Steroid Biochem Mol Biol Dec. 2002;83(1-5):195-197.
Couse, Estrogen Receptor Null Mice: What Have We Learned and Where Will They Lead Us? Endocr Rev Jun. 1999;20(3):358-417.
Evans, The steroid and thyroid hormone receptor superfamily. Science May 13, 1988;240(4854):889-895.
Green, Human oestrogen receptor cDNA: sequence, expression and homology to v-erb-A. Nature Mar. 13-19, 1986;320(6058):134-139.
Greene, Sequence and expression of human estrogen receptor complementary DNA. Science Mar. 7, 1986;231 (4742):1150-1154.
Harris et al., Evaluation of an Estrogen Receptor-beta Agonist in Animal Models of Human Disease. Endocrinology. Oct. 2003;144(10):4241-4249.
Hewitt et al., Estrogen receptor transcription and transactivation Estrogen receptor knockout mice: what their phenotypes reveal about mechanisms of estrogen action. Breast Cancer Res 2000;2(5):345-352.
Koehler et al., Reflections on the Discovery and Significance of Estrogen Receptor beta. Endocr Reviews, May 2005;26(3):465-478.
Kuiper and Gustafsson, The novel estrogen receptor-beta subtype: potential role in the cell- and promoter-specific actions of estrogens and anti-estrogens. Febs Lett, Jun. 23, 1997;410(1):87-90.
Kuiper et al., Cloning of a novel estrogen receptor expressed in rat prostate and ovary. Proc Natl Acad Sci U S A. Jun. 11, 1996;93(12):5925-5930.
Lindberg et al., Two Different Pathways for the Maintenance of Trabecular Bone in Adult Male Mice. J Bone Miner Res Apr. 2002;17(4):555-562.
Matthews and Gustafsson, Estrogen signaling: a subtle balance between ER alpha and ER beta. Mol Interv. 2003;3(5):281-292.
Nilsson and Koehler, Oestrogen Receptors and Selective Oestrogen Receptor Modulators: Molecular and Cellular Pharmacology. Basic Clin Pharmacol Toxicol. Jan. 2005;96(1):15-25.
Osborne and Schiff, Estrogen-Receptor Biology: Continuing Progress and Therapeutic Implications. J Clin Oncol Mar. 10, 2005;23(8):1616-1622.
Osterlund and Hurd, Estrogen receptors in the human forebrain and the relation to neuropsychiatric disorders. Prog Neurobiol Jun. 2001;64(3):251-267.
Ostlund et al., Estrogen receptor gene expression in relation to neuropsychiatric disorders. Ann NY Acad Sci Dec. 2003;1007:54-63.

(Continued)

Primary Examiner — Taofiq A Solola
(74) Attorney, Agent, or Firm — Sam K. Tahmassebi; TechLaw LLP

(57) ABSTRACT

Disclosed herein are compounds of Formula I

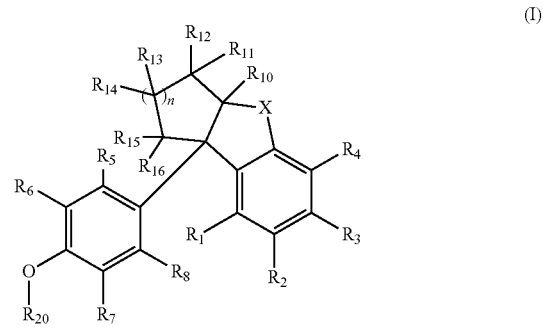

(I)

as disclosed herein, methods of modulating the activity of an estrogen receptor and methods of treating a disorder associated with estrogen receptors.

26 Claims, No Drawings

OTHER PUBLICATIONS

Patrone, Regulation of Postnatal Lung Development and Homeostasis by Estrogen Receptor beta. Mol Cell Biol. Dec. 2003;23(23):8542-8552.

Piu et al., Dissection of the cytoplasmic domains of cytokine receptors involved in STAT and Ras dependent proliferation. Oncogene May 16 2002;21(22):3579-3591.

Piu et al., Identification of novel subtype selective RAR agonists. Biochem Pharmacol. Dec. 19, 2005;71(1-2):156-162.

Piu et al., beta-arrestin 2 modulates the activity of nuclear receptor RAR beta2 through activation of ERK2 kinase. Oncogene. Jan. 12, 2006;25(2):218-229.

Wang, Morphological abnormalities in the brains of estrogen receptor beta knockout mice. Proc Natl Acad Sci U S A. Feb. 27, 2001;98(5):2792-2796.

Wang, Estrogen receptor (ER)beta knockout mice reveal a role for ERbeta in migration of cortical neurons in the developing brain. Proc Natl Acad Sci U S A. Jan. 21, 2003;100(2):703-708.

Windahl, Elucidation of estrogen receptor function in bone with the use of mouse models. Trends Endocrinol Metab, Jul. 2002;13(5):195-200.

Wise, Estrogens and neuroprotection. Trends Endocrinol Metab Aug. 2002;13(6):229-230.

Brauner-Osbome and Brann, Pharmacology of muscarinic acetylcholine receptor subtypes (m1-m5): high throughput assays in mammalian cells, Eur J Pharm 295 (1996) 93-102.

* cited by examiner

COMPOUNDS WITH ACTIVITY AT ESTROGEN RECEPTORS

RELATED APPLICATIONS

The present application is a divisional of U.S. application Ser. No. 12/258,313, filed on Oct. 24, 2008 by Olsson et al., and entitled "COMPOUNDS WITH ACTIVITY AT ESTROGEN RECEPTORS", which in turn claims priority to the U.S. Provisional Application Ser. No. 60/983,078, filed on Oct. 26, 2007 by Olsson et al., and entitled "COMPOUNDS WITH ACTIVITY AT ESTROGEN RECEPTORS", the entire disclosure of both of which is hereby incorporated by reference herein.

FIELD OF THE INVENTION

This invention relates to the fields of organic chemistry, pharmaceutical chemistry, biochemistry, molecular biology and medicine. In particular it relates to compounds that modulate the activity of the Estrogen receptors, and to the use of the compounds for the treatment and prevention of diseases and disorders related to the Estrogen beta receptor.

BACKGROUND OF THE DISCLOSURE

Estrogen receptors (ER) belong to the family of nuclear hormone receptors. Nuclear hormone receptors define a superfamily of ligand-activated transcription factors (Evans, 1988, Science 240:889). Members of this family are typically characterized by the presence of conserved modular domains: a zinc finger DNA-binding domain (DBD) triggers the interaction of the receptor with specific response elements at the DNA site, a ligand-binding domain (LBD) adjacent to the DBD, and two transcriptional activation domains AF-1 and AF-2 ligand independent and ligand dependent, respectively (Nilsson, 2002, SERMs: Research and clinical applications, Eds: Humana Press Inc, 3). Upon ligand binding to the receptor, a conformational change occurs within the LBD bringing the AF-2 domain in closer proximity and allowing for the recruitment of co-activators. Co-activators create a physical interaction between the nuclear-hormone receptor and components of the transcriptional machinery, establishing transcriptional modulation of target genes.

Two estrogen receptor subtypes have been identified: ER alpha (ERα, NR3A1) (Green, 1986, Nature 320:134; Greene, 1986, Science 231:1150) and ER beta (ERβ, NR3A2) (Kuiper, 1996, PNAS 93:5925). Both receptors bind to the endogenous natural ligand 17β estradiol with comparable high affinity and modulate the transcriptional activity of target genes through classical estrogen response elements (reviewed in Nilsson, 2005, Bas Clin Pharm Tox, 96:15). More recently, it has been demonstrated that estrogen receptors can mediate non classical actions (reviewed in Osborne, 2005, J Clin Oncol 8:1616): (1) non-classical transcriptional regulation in which ERs function as co-activators on alternate regulatory DNA sequences, (2) non genomic or membrane-initiated steroid signaling in which ERs evoke rapid cytoplasmic signaling, and (3) crosstalk with Receptor Tyrosine Kinases (RTKs). Interestingly, their ligand binding domains (LBD) only share 56% amino acid identity which suggest that they might accommodate different ligands and thus mediate different or even opposite effects (Kuiper, 1997, FEBS Lett, 410:87). Moreover, the distribution pattern of the two receptors is quite different (reviewed in Mathews, 2003, Mol Intery 3:281). Both ERs are widely distributed both peripherally and in the brain, displaying distinct and sometimes overlapping patterns in a variety of tissues. ERα is expressed primarily in the uterus, liver, kidney and heart. On the other hand ERβ is present mainly in the ovary, prostate, lung, gastrointestinal tract, bladder, hematopoietic and central nervous system (CNS). ERβ specific localization in the CNS includes the hippocampus and thalamus (Osterlund, 2001, Prog Neurobiol 64:251; Ostlund, 2003, Ann NY Acad Sci 1007:54). ERα and ERβ are co-expressed in the mammary gland, epididymis, thyroid, adrenal, bone and the dorsal root ganglia of the spinal cord and the cerebral cortex of the brain.

The characterization of mice lacking ERα or ERβ has provided insight into the physiology of estrogen receptors (reviewed in Hewitt, 2000, Breast Cancer Res 2:345; Couse, 1999, Endoc Rev 20:358). Both ERα male and female null mice are infertile because of dysfunction in spermatogenesis and ovulation, respectively. In addition, null females display a lack of sexual behavior, increased aggression and infanticide. Null male exhibit normal mounting behavior but a complete lack of intromission and ejaculation. They also show reduced aggression. In contrast, ERβ null female mice are subfertile with reduced littermates. Male counterparts show no apparent defects in their reproductive tract. The neuroendocrine system is significantly altered in ERα null mice in contrast to ERβ null mice which do not show any impairment. Moreover, the knock-out of ERα in mice leads to absence of breast tissue development, lower bone density and impaired glucose tolerance. Knock out studies of ERβ led to controversial results with some studies being unable to see an effect on bone density (Lindberg, 2002, J Bone Min Res 17:555), whereas other reports suggested an increase in trabecular bone volume in females only due to decreased bone resorption (reviewed in Windahl, 2002, Trends Endoc Metab, 13:195). Interestingly, morphological alterations in the brains of mice lacking ERβ are evident (Wang, 2001, PNAS 98:2792) including an association with impaired neuronal survival (Wang, 2003, PNAS 100:703). This has led to speculation that ERβ could have an important role in protecting from neurodegenerative disorders such as Alzheimer and Parkinson diseases, and potentially those resulting from trauma and cardiovascular insults. This hypothesis is further supported by experimental studies indicating a neurotrophic and neuroprotective role for estrogens (reviewed in Wise, 2002, Trends Endocrinol Metab 13:229; Behl, 2003, J Steroid Biochem Mol Biol 83:195).

More recently, the use of a relatively selective ERβ agonist has unraveled a prominent role in inflammation for this subtype (Harris, 2003, Endoc 144:4241). Beneficial effects were seen in animal models of inflammatory bowel disease and adjuvant-induced arthritis. Indeed, ERβ is expressed both in the intestine and in immune cells. Moreover, ERβ null studies have suggested a role in thymus function (Erlandsson, 2001, Immunol 103:17) as well as in pulmonary inflammation (Patrone, 2003, Mol Cell Biol 25:8542). Interestingly, though, no effects associated with classical estrogen function were evident through the use of this ERβ agonist (Harris, 2003, Endoc 144:4241). In particular, that ligand was inactive in mammotrophy, bone density and ovulation in in vivo assays. This data is contrary, to a certain extent, to a variety of studies including human polymorphisms, knock-out animals, and tissue distribution that argue for a role of ERβ in bone and ovulation homeostasis. Other proposed therapeutic roles for selective ERβ agonists include prostate and breast cancer, autoimmune diseases, colon cancer, malignancies of the immune system, neurodegeneration, cardiovascular function, and bone function (reviewed in Koehler, 2005, Endocr Reviews, DOI 10.1210). Several ERβ agonists are discussed in the International Publications WO 2005/108337 and WO 2007/0565500.

SUMMARY OF THE INVENTION

Disclosed herein are compounds of Formula I:

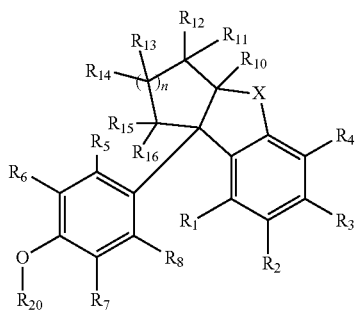

(I)

or a pharmaceutically acceptable salt or metabolite thereof, wherein:

X is selected from the group consisting of oxygen, sulfur, S=O, $SO_2$, $NR_{30}$, $CR_{31}R_{32}$;

n is an integer selected from the group consisting of 1, 2, 3 and 4

$R_{20}$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heteroalicyclyl, haloalkyl, perhaloalkyl, sulphonyl, —C(=Z)$R_{30}$, —C(=Z)O$R_{30}$, —C(=Z)N$R_{31}R_{32}$, —S(O)N$R_{31}R_{32}$, —S(O)$_2$N$R_{31}R_{32}$, —P(=O)(O$R_{30}$), and —CH$_2$O(C=O)$R_{30}$;

$R_1$, $R_2$, $R_3$, and $R_4$ are each separately and independently selected from the group consisting of hydrogen, $C_{1-6}$alkyl, $C_{2-6}$alkenyl, $C_{2-6}$alkynyl, $C_{3-6}$cycloalkyl, $C_{1-6}$alkyl($C_{3-6}$cycloalkyl), halogen, $C_{1-6}$haloalkyl, $C_{1-6}$ perhaloalkyl, $C_{1-6}$haloalkoxy, —CN, —C(=Z)$R_{30}$, —C(=Z)O$R_{30}$, —C(=Z)N$R_{31}R_{32}$, —C($R_{30}$)=N$R_{31}$, —N$R_{31}R_{32}$, —N=C$R_{31}R_{32}$, —N($R_{30}$)—C(=Z)$R_{30}$, —N($R_{30}$)—C(=Z)N$R_{31}R_{32}$, —S(O)N$R_{31}R_{32}$, —S(O)$_2$N$R_{31}R_{32}$, —N($R_{30}$)—S(=O)$R_{30}$, —N($R_{30}$)—S(=O)$_2R_{30}$, —O$R_{30}$, —S$R_{30}$, and —OC(=Z)$R_{30}$; wherein said alkyl, alkenyl, alkynyl, cycloalkyl and alkoxy are optionally substituted;

or two of $R_1$, $R_2$, $R_3$, and $R_4$ on adjacent carbons taken together, along with the two intervening carbons to which they are attached, form a $C_{3-6}$cycloalkenyl, aryl, heteroaryl or $C_{3-6}$heterocycloalkenyl group;

$R_5$, $R_6$, $R_7$, and $R_8$ are each separately and independently selected from the group consisting of hydrogen, $C_{1-6}$alkyl, $C_{2-6}$alkenyl, $C_{2-6}$alkynyl, $C_{3-6}$cycloalkyl, $C_{1-6}$alkyl($C_{3-6}$cycloalkyl), halogen, $C_{1-6}$haloalkyl, $C_{1-6}$ perhaloalkyl, $C_{1-6}$haloalkoxy, —CN, —C(=Z)$R_{30}$, —C(=Z)O$R_{30}$, —C(=Z)N$R_{31}R_{32}$, —C($R_{30}$)=N$R_{31}$, —N$R_{31}R_{32}$, —N=C$R_{31}R_{32}$, —N($R_{30}$)—C(=Z)$R_{30}$, —N($R_{30}$)—C(=Z)N$R_{31}R_{32}$, —S(O)N$R_{31}R_{32}$, —S(O)$_2$N$R_{31}R_{32}$, —N($R_{30}$)—S(=O)$R_{30}$, —N($R_{30}$)—S(=O)$_2R_{30}$, —O$R_{30}$, —S$R_{30}$, and —OC(=Z)$R_{30}$; wherein said alkyl, alkenyl, alkynyl, cycloalkyl and alkoxy are optionally substituted;

or two of $R_5$, $R_6$, $R_7$, and $R_8$ on adjacent carbons taken together, along with the two intervening carbons to which they are attached, form a $C_{3-6}$cycloalkenyl, aryl, heteroaryl or $C_{3-6}$heterocycloalkenyl group $R_{10}$, $R_{11}$, $R_{12}$, $R_{13}$, $R_{14}$, $R_{15}$, and $R_{16}$ are each separately and independently selected from the group consisting of hydrogen, $C_{1-6}$alkyl, $C_{2-6}$alkenyl, $C_{2-6}$alkynyl, $C_{3-6}$cycloalkyl, $C_{1-6}$alkyl($C_{3-6}$cycloalkyl), halogen, $C_{1-6}$haloalkyl, $C_{1-6}$ perhaloalkyl, $C_{1-6}$haloalkoxy, —CN, —C(=Z)$R_{30}$, —C(=Z)O$R_{30}$, —C(=Z)N$R_{31}R_{32}$, —C($R_{30}$)=N$R_{31}$, —N$R_{31}R_{32}$, —N=C$R_{31}R_{32}$, —N($R_{30}$)—C(=Z)$R_{30}$, —N($R_{30}$)—C(=Z)N$R_{31}R_{32}$, —S(O)N$R_{31}R_{32}$, —S(O)$_2$N$R_{31}R_{32}$, —N($R_{30}$)—S(=O)$R_{30}$, —N($R_{30}$)—S(=O)$_2R_{30}$, —O$R_{30}$, —S$R_{30}$, and —OC(=Z)$R_{30}$; wherein said alkyl, alkenyl, alkynyl, cykloalkyl and alkoxy is optionally substituted;

or two geminal $R_{11}$, $R_{12}$, $R_{13}$, $R_{14}$, $R_{15}$, and $R_{16}$ taken together, along with the carbon atom to which they are attached, form a carbonyl group;

or two geminal $R_{11}$, $R_{12}$, $R_{13}$, $R_{14}$, $R_{15}$, and $R_{16}$ taken together, along with the carbon atom to which they are attached, form a $C_{3-6}$cycloalkyl or $C_{2-6}$heterocycloalkyl group;

or two geminal $R_{11}$, $R_{12}$, $R_{13}$, $R_{14}$, $R_{15}$, and $R_{16}$ taken together, along with the carbon atom to which they are attached, form a $C_{2-6}$alkylidenegroup or two $R_{10}$, $R_{11}$, $R_{12}$, $R_{13}$, $R_{14}$, $R_{15}$, and $R_{16}$ on adjacent carbons, taken together along with the two intervening carbon atoms to which they are attached, form a double bond;

or one of $R_{10}$, $R_{11}$, $R_{12}$, $R_{13}$, $R_{14}$, $R_{15}$, and $R_{16}$ and the carbon atom to which it is attached and the carbon atom to which one adjacent $R_{10}$, $R_{11}$, $R_{12}$, $R_{13}$, $R_{14}$, $R_{15}$, and $R_{16}$ is attached, form a $C_{3-6}$cycloalkyl or $C_{2-6}$heterocycloalkyl group, provided that one or more of $R_{10}$-$R_{16}$ is not present to complete the octet of all carbon atoms;

or one of $R_{10}$, $R_{11}$, $R_{12}$, $R_{13}$, $R_{14}$, $R_{15}$, and $R_{16}$ and the carbon atom to which it is attached and the carbon atom to which one non-adjacent $R_{10}$, $R_{11}$, $R_{12}$, $R_{13}$, $R_{14}$, $R_{15}$, and $R_{16}$ is attached, taken together with all intervening carbon atoms, form a $C_{3-6}$cycloalkyl or $C_{2-6}$heterocycloalkyl group, provided that one or more of $R_{10}$-$R_{16}$ is not present to complete the octet of all carbon atoms;

or one of $R_5$, $R_6$, $R_7$, and $R_8$ and the carbon atom to which it is attached and the carbon atom to which one of $R_{10}$, $R_{11}$, $R_{12}$, $R_{13}$, $R_{14}$, $R_{15}$, and $R_{16}$ is attached and at least two intervening carbon atoms, or one of $R_{10}$, $R_{11}$, $R_{12}$, $R_{13}$, $R_{14}$, $R_{15}$, and $R_{16}$ and the carbon atom to which it is attached and the carbon atom to which one of $R_5$, $R_6$, $R_7$, and $R_8$ is attached and at least two intervening carbon atoms, form a $C_{5-7}$cycloalkenyl or $C_{4-7}$heterocycloalkyl group, provided that one or more of $R_5$-$R_{16}$ is not present to complete the octet of all carbon atoms;

Z is oxygen or sulfur; and $R_{30}$, $R_{31}$ and $R_{32}$ are each independently selected from the group consisting of hydrogen, optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{3-6}$cycloalkenyl, optionally substituted aryl, optionally substituted heteroaryl, optionally substituted $C_{2-6}$heteroalicyclyl.

or $R_{31}$ and $R_{32}$ taken together, along with the nitrogen atom to which they are attached, form a heterocycloalkyl group;

or $R_{31}$ and $R_{32}$ taken together, along with the carbon atom to which they are attached, form a $C_{3-6}$cycloalkyl or heterocycloalkyl group.

Also disclosed herein are pharmaceutical compositions comprising one or more compounds of Formula I and a pharmaceutically acceptable diluents, excipient, or carrier.

Also disclosed herein are methods of modulating or specifically agonizing one or more Estrogen receptors, reducing inflammation, treating neuropathic pain, treating allergic conjunctivitis, reducing IL-4 levels, decreasing IFN-γ levels, treating dry eye, increasing IL-12 levels, hormonal replacement therapy, lowering cholesterol, triglycerides, or LDL levels, treating impaired cognition or providing neuroprotection, preventing conception, treating or preventing disorders selected from the group consisting of inflammatory bowel syndrome; Crohn's disease; ulcerative proctitis or colitis; prostatic hypertrophy; uterine leiomyomnas; breast carcinoma; endometrial carcinoma; polycystic ovary syndrome; endometrial polyps; benign breast disease; adenomyosis; ovarian carcinoma; melanoma; prostate carcinoma; colon carcinoma; brain tumors including glioblastoma, astrocytoma, glioma, or meningioma; prostatitis; interstitial cystitis; bone density loss including osteoporosis or osteopenia; discholesterolemia; dislipidemia; cardiovascular disease; atherosclerosis; hypertension; peripheral vascular disease; restenosis; vasospasm; neurodegenerative disorders including Alzheimer's disease, Huntington's disease, Parkinson's disease or other dementias; cognitive decline; stroke; anxiety; vaginal atrophy; vulvar atrophy; atrophic vaginitis; vaginal dryness; pruritus; dyspareunia; frequent urination; urinary incontinence; urinary tract infections; vasomotor symptoms including flusing or hot flashes; arthritis including rheumatoid arthritis, osteoarthritis, or arthropathiesendometriosis; psoriasis; dermatitis; asthma; pleurisy; multiple sclerosis; systemic lupus erthematosis; uveitis; sepsis; hemmorhagic shock; type II diabetes; acute or chronic inflammation; acute or chronic pain; lung disorders including asthma or chronic obstructive pulmonary disease; ophthalmologic disorders including glaucoma, dry eye, or macular degeneration; free radical induced disease states; and cancer selected from the group consisting of colorectal cancer, prostate cancer, breast cancer, ovarian cancer, endometrial cancer, and uterine cancer; in a subject, comprising: identifying a subject in need thereof, and administering to the subject an effective amount of one or more compounds of Formula I.

DETAILED DESCRIPTION OF THE EMBODIMENTS

In one aspect, disclosed herein are compounds of Formula I:

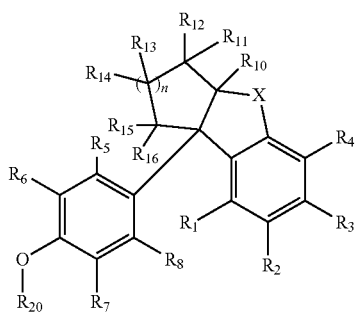

(I)

or a pharmaceutically acceptable salt or metabolite thereof, wherein:

X is selected from the group consisting of oxygen, sulfur, S=O, $SO_2$, $NR_{30}$, $CR_{31}R_{32}$;

n is an integer selected from the group consisting of 1, 2, 3 and 4

$R_{20}$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heteroalicyclyl, haloalkyl, perhaloalkyl, sulphonyl, —C(=Z)$R_{30}$, —C(=Z)$OR_{30}$, —C(=Z)$NR_{31}R_{32}$, —S(O)$NR_{31}R_{32}$, —S(O)$_2NR_{31}R_{32}$, —P(=O)(OR$_{30}$), and —CH$_2$O(C=O)$R_{30}$;

$R_1$, $R_2$, $R_3$, and $R_4$ are each separately and independently selected from the group consisting of hydrogen, $C_{1-6}$alkyl, $C_{2-6}$alkenyl, $C_{2-6}$alkynyl, $C_{3-6}$cycloalkyl, $C_{1-6}$alkyl($C_{3-6}$cycloalkyl), halogen, $C_{1-6}$haloalkyl, $C_{1-6}$ perhaloalkyl, $C_{1-6}$haloalkoxy, —CN, —C(=Z)$R_{30}$, —C(=Z)$OR_{30}$, —C(=Z)$NR_{31}R_{32}$, —C($R_{30}$)=$NR_{31}$, —$NR_{31}R_{32}$, —N=$CR_{31}R_{32}$, —N($R_{30}$)—C(=Z)$R_{30}$, —N($R_{30}$)—C(=Z)$NR_{31}R_{32}$, —S(O)$NR_{31}R_{32}$, —S(O)$_2NR_{31}R_{32}$, —N($R_{30}$)—S(=O)$R_{30}$, —N($R_{30}$)—S(=O)$_2R_{30}$, —$OR_{30}$, —$SR_{30}$, and —OC(=Z)$R_{30}$; wherein said alkyl, alkenyl, alkynyl, cycloalkyl and alkoxy are optionally substituted;

or two of $R_1$, $R_2$, $R_3$, and $R_4$ on adjacent carbons taken together, along with the two intervening carbons to which they are attached, form a $C_{3-6}$cycloalkenyl, aryl, heteroaryl or $C_{3-6}$heterocycloalkenyl group;

$R_5$, $R_6$, $R_7$, and $R_8$ are each separately and independently selected from the group consisting of hydrogen, $C_{1-6}$alkyl, $C_{2-6}$alkenyl, $C_{2-6}$alkynyl, $C_{3-6}$cycloalkyl, $C_{1-6}$alkyl($C_{3-6}$cycloalkyl), halogen, $C_{1-6}$haloalkyl, $C_{1-6}$ perhaloalkyl, $C_{1-6}$haloalkoxy, —CN, —C(=Z)$R_{30}$, —C(=Z)$OR_{30}$, —C(=Z)$NR_{31}R_{32}$, —C($R_{30}$)=$NR_{31}$, —$NR_{31}R_{32}$, —N=$CR_{31}R_{32}$, —N($R_{30}$)—C(=Z)$R_{30}$, —N($R_{30}$)—C(=Z)$NR_{31}R_{32}$, —S(O)$NR_{31}R_{32}$, —S(O)$_2NR_{31}R_{32}$, —N($R_{30}$)—S(=O)$R_{30}$, —N($R_{30}$)—S(=O)$_2R_{30}$, —$OR_{30}$, —$SR_{30}$, and —OC(=Z)$R_{30}$; wherein said alkyl, alkenyl, alkynyl, cycloalkyl and alkoxy are optionally substituted;

or two of $R_5$, $R_6$, $R_7$, and $R_8$ on adjacent carbons taken together, along with the two intervening carbons to which they are attached, form a $C_{3-6}$cycloalkenyl, aryl, heteroaryl or $C_{3-6}$heterocycloalkenyl group $R_{10}$, $R_{11}$, $R_{12}$, $R_{13}$, $R_{14}$, $R_{15}$, and $R_{16}$ are each separately and independently selected from the group consisting of hydrogen, $C_{1-6}$alkyl, $C_{2-6}$alkenyl, $C_{2-6}$alkynyl, $C_{3-6}$cycloalkyl, $C_{1-6}$alkyl($C_{3-6}$cycloalkyl), halogen, $C_{1-6}$haloalkyl, $C_{1-6}$ perhaloalkyl, $C_{1-6}$haloalkoxy, —CN, —C(=Z)$R_{30}$, —C(=Z)$OR_{30}$, —C(=Z)$NR_{31}R_{32}$, —C($R_{30}$)=$NR_{31}$, —$NR_{31}R_{32}$, —N=$CR_{31}R_{32}$, —N($R_{30}$)—C(=Z)$R_{30}$, —N($R_{30}$)—C(=Z)$NR_{31}R_{32}$, —S(O)$NR_{31}R_{32}$, —S(O)$_2NR_{31}R_{32}$, —N($R_{30}$)—S(=O)$R_{30}$, —N($R_{30}$)—S(=O)$_2R_{30}$, —$OR_{30}$, —$SR_{30}$, and —OC(=Z)$R_{30}$; wherein said alkyl, alkenyl, alkynyl, cykloalkyl and alkoxy is optionally substituted;

or two geminal $R_{11}$, $R_{12}$, $R_{13}$, $R_{14}$, $R_{15}$, and $R_{16}$ taken together, along with the carbon atom to which they are attached, form a carbonyl group;

or two geminal $R_{11}$, $R_{12}$, $R_{13}$, $R_{14}$, $R_{15}$, and $R_{16}$ taken together, along with the carbon atom to which they are attached, form a $C_{3-6}$cycloalkyl or $C_{2-6}$heterocycloalkyl group;

or two geminal $R_{11}$, $R_{12}$, $R_{13}$, $R_{14}$, $R_{15}$, and $R_{16}$ taken together, along with the carbon atom to which they are attached, form a $C_{2-6}$alkylidenegroup or two $R_{10}$, $R_{11}$, $R_{12}$, $R_{13}$, $R_{14}$, $R_{15}$, and $R_{16}$ on adjacent carbons, taken together along with the two intervening carbon atoms to which they are attached, form a double bond;

or one of $R_{10}$, $R_{11}$, $R_{12}$, $R_{13}$, $R_{14}$, $R_{15}$, and $R_{16}$ and the carbon atom to which it is attached and the carbon atom to which one adjacent $R_{10}$, $R_{11}$, $R_{12}$, $R_{13}$, $R_{14}$, $R_{15}$, and $R_{16}$ is attached, form a $C_{3-6}$cycloalkyl or $C_{2-6}$heterocycloalkyl group, provided that one or more of $R_{10}$-$R_{16}$ is not present to complete the octet of all carbon atoms;

or one of $R_{10}$, $R_{11}$, $R_{12}$, $R_{13}$, $R_{14}$, $R_{15}$, and $R_{16}$ and the carbon atom to which it is attached and the carbon atom to which one non-adjacent $R_{10}$, $R_{11}$, $R_{12}$, $R_{13}$, $R_{14}$, $R_{15}$, and $R_{16}$ is attached, taken together with all intervening carbon atoms, form a $C_{3-6}$cycloalkyl or $C_{2-6}$heterocycloalkyl group, provided that one or more of $R_{10}$-$R_{16}$ is not present to complete the octet of all carbon atoms;

or one of $R_5$, $R_6$, $R_7$, and $R_8$ and the carbon atom to which it is attached and the carbon atom to which one of $R_{10}$, $R_{11}$, $R_{12}$, $R_{13}$, $R_{14}$, $R_{15}$, and $R_{16}$ is attached and at least two intervening carbon atoms, or one of $R_{10}$, $R_{11}$, $R_{12}$, $R_{13}$, $R_{14}$, $R_{15}$, and $R_{16}$ and the carbon atom to which it is attached and the carbon atom to which one of $R_5$, $R_6$, $R_7$, and $R_8$ is attached and at least two intervening carbon atoms, form a $C_{5-7}$cycloalkenyl or $C_{4-7}$heterocycloalkyl group, provided that one or more of $R_5$-$R_{16}$ is not present to complete the octet of all carbon atoms;

Z is oxygen or sulfur; and $R_{30}$, $R_{31}$ and $R_{32}$ are each independently selected from the group consisting of hydrogen, optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{3-6}$cycloalkenyl, optionally substituted aryl, optionally substituted heteroaryl, optionally substituted $C_{2-6}$heteroalicyclyl;

or $R_{31}$ and $R_{32}$ taken together, along with the nitrogen atom to which they are attached, form a heterocycloalkyl group;

or $R_{31}$ and $R_{32}$ taken together, along with the carbon atom to which they are attached, form a $C_{3-6}$cycloalkyl or heterocycloalkyl group.

Unless otherwise specified, "R" group(s) such as, without limitation, R, $R^a$ and $R^b$, is(are) independently selected from the group consisting of hydrogen, alkyl, alkenyl, alkynyl, cycloalkyl, aryl, heteroaryl (bonded to the indicated group at a ring carbon atom) and heteroalicyclyl (likewise bonded to the indicated group at a ring carbon atom), as these groups are defined herein. If two "R" groups are covalently bonded to the same atom then they may be bound together so as to form a cycloalkyl or heteroalicyclyl group.

Unless otherwise indicated, when a substituent is deemed to be "optionally substituted" it is meant that the substituent is a group that may be substituted with one or more group(s) individually and independently selected, without limitation, from alkyl, alkenyl, alkynyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is incorporated herein in its entirety.

As used herein, "$C_m$-$C_n$" in which "m" and "n" are integers refers to the number of carbon atoms in an alkyl, alkenyl or alkynyl group, or the number of carbon atoms in the ring of a cycloalkyl, cycloalkenyl, or aryl group, or the number of carbon atoms in the ring of a heteroaryl, heterocycloalkyl, or heterocycloalkenyl group. That is, the alkyl, alkenyl, alkynyl, ring of the cycloalkyl, ring of the cycloalkenyl, or of the aryl can contain from "m" to "n", inclusive, carbon atoms. Thus, for example, a "$C_1$-$C_4$ alkyl" group refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$—, and $(CH_3)_3CH$—. If no "m" and "n" are designated with regard to an alkyl, alkenyl, alkynyl, cycloalkyl or cycloalkenyl group, the broadest range described in these definitions is to be assumed.

As used herein, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Examples of aryl groups include, without limitation, benzene, naphthalene and azulene.

As used herein, "heteroaryl" refers to a ring that has a fully delocalized pi-electron system and contains one or more heteroatoms selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "alkyl" refers to a straight or branched chain fully saturated (no double or triple bonds) hydrocarbon group. An alkyl group of this invention may comprise from 1 to 20 carbon atoms, that is, m=1 and n=20. An alkyl group herein may also be of medium size having 1 to 10 carbon atoms. An alkyl group herein may also be a lower alkyl having 1 to 5 carbon atoms. Examples of alkyl groups include, without limitation, methyl, ethyl, n-propyl, isopropyl, n-butyl, iso-butyl, sec-butyl, tert-butyl, amyl, tert-amyl, hexyl, heptyl, octyl, nonyl, decyl, undecyl and dodecyl.

An alkyl group of this invention may be substituted or unsubstituted. When substituted, the substituent group(s) can be one or more group(s) independently selected from cycloalkyl, aryl, heteroaryl, heteroalicyclyl, hydroxy, protected hydroxyl, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, —$NR^aR^b$ and protected amino.

As used herein, "alkenyl" refers to an alkyl group that contains in the straight or branched hydrocarbon chain one or more double bonds. An alkenyl group of this invention may be unsubstituted or substituted. When substituted, the substituent(s) may be selected from the same groups disclosed above with regard to alkyl group substitution, or with regard to optional substitution.

As used herein, "alkynyl" refers to an alkyl group that contains in the straight or branched hydrocarbon chain one or more triple bonds. An alkynyl group of this invention may be unsubstituted or substituted. When substituted, the substituent(s) may be selected from the same groups disclosed above with regard to alkyl group substitution, or with regard to optional substitution.

As used herein, "acyl" refers to an "RC(=O)—" group with R as defined above.

As used herein, "cycloalkyl" refers to a completely saturated (no double bonds) hydrocarbon ring. Cycloalkyl groups of this invention may range from $C_3$ to $C_8$. A cycloalkyl group may be unsubstituted or substituted. If substituted, the substituent(s) may be selected from those indicated above with regard to substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heteroalicyclic.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of this invention may be unsubstituted or substituted. When substituted, the substituent(s) may be selected from the same groups disclosed above with regard to alkyl group substitution. The "cycloalkenyl" group can be made up of two or more fused rings (rings that share two adjacent carbon atoms). When the cycloalkenyl is a fused ring system, then the ring that is connected to the rest of the molecule is a cycloalkenyl as defined above. The other ring(s) in the fused ring system may be a cycloalkyl, a cycloalkenyl, an aryl, a heteroaryl, or a heteroalicyclic.

The term "alkylene" refers to an alkyl group, as defined herein, which is a biradical and is connected to two other moieties. Thus, methylene (—$CH_2$—), ethylene (—$CH_2CH_2$—), proylene (—$CH_2CH_2CH_2$—), isopropylene (—$CH_2$—$CH(CH_3)$—), and isobutylene (—$CH_2$—CH($CH_3$)—$CH_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "heterocycloalkyl," "heteroalicyclic," or "heteroalicyclyl" refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heteroalicyclyl groups of this invention may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethanesulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heteroalicyclic.

An "O-carboxy" group refers to a "RC(=O)O—" group with R as defined above.

A "C-carboxy" group refers to a "—C(=O)R" group with R as defined above.

An "acetyl" group refers to a $CH_3C$(=O)— group.

A "trihalomethanesulfonyl" group refers to an "$X_3CSO_2$—" group wherein X is a halogen.

A "cyano" group refers to a "—CN" group.

An "isocyanato" group refers to an "—NCO" group.

A "thiocyanato" group refers to a "—CNS" group.

An "isothiocyanato" group refers to an "—NCS" group.

A "sulfinyl" group refers to an "—S(=O)—R" group with R as defined above.

A "sulfonyl" group refers to an "$SO_2R$" group with R as defined above.

An "S-sulfonamido" group refers to a "—$SO_2NR^aR^b$" group with $R^a$ and $R^b$ as defined above.

An "N-sulfonamido" group refers to a "$RSO_2N(R^a)$—" group with R and $R^a$ as defined above.

A "trihalomethanesulfonamido" group refers to an "$X_3CSO_2N(R)$—" group with X as halogen and R as defined above.

An "O-carbamyl" group refers to a "—OC(=O)$NR^aR^b$" group with $R^a$ and $R^b$ as defined above.

An "N-carbamyl" group refers to an "ROC(=O)$NR^a$—" group with $R^a$ and R as defined above.

An "O-thiocarbamyl" group refers to a "—OC(=S)—$NR^aR^b$" group with $R^a$ and $R^b$ as defined above.

An "N-thiocarbamyl" group refers to an "ROC(=S)$NR^a$—" group with $R^a$ and R as defined above.

A "C-amido" group refers to a "—C(=O)$NR^aR^b$" group with $R^a$ and $R^b$ as defined above.

An "N-amido" group refers to a "RC(=O)$NR^a$—" group with R and $R^a$ as defined above.

The term "perhaloalkyl" refers to an alkyl group in which all the hydrogen atoms are replaced by halogen atoms.

As used herein, an "ester" refers to a "—C(=O)OR" group with R as defined above.

As used herein, an "amide" refers to a "—C(=O)$NR^aR^b$" group with $R^a$ and $R^b$ as defined above.

Any unsubstituted or monosubstituted amine group on a compound herein can be converted to an amide, any hydroxyl group can be converted to an ester and any carboxyl group can be converted to either an amide or ester using techniques well-known to those skilled in the art (see, for example, Greene and Wuts, Protective Groups in Organic Synthesis, $3^{rd}$ Ed., John Wiley & Sons, New York, N.Y., 1999).

As used herein, when two substituents taken together, along with the nitrogen atom to which they are attached, form a heterocycloalkyl or a heteroaryl group, it is meant that the groups may be joined to form a, heteroaryl or heteroalicyclyl group. For example, without limitation, if $R^a$ and $R^b$ of an $NR^aR^b$ group are indicated that taken together, along with the nitrogen atom to which they are attached, form a heterocycloalkyl or a heteroaryl group, it is meant that they are covalently bonded to one another at their terminal atoms to form a ring, such that —$NR^aR^b$ forms a

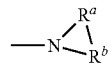

As used herein, when two geminal substituents taken together, along with the carbon atom to which they are attached, form a carbonyl group, it is meant that, for example,

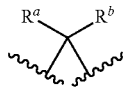

forms a

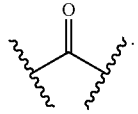

As used herein, when two geminal substituents taken together, along with the carbon atom to which they are attached, form a cycloalkyl or a heterocycloalkyl group, it is meant that, for example,

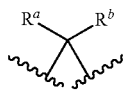

forms a

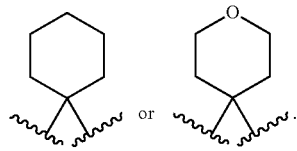 [SMILES: *C1(*)CCCCC1 ; *C1(*)CCOCC1]

As used herein, when two substituents on adjacent carbons taken together, along with the two intervening carbon atoms to which they are attached, form a double bond, it is meant that, for example,

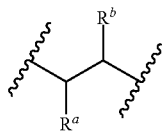

forms a

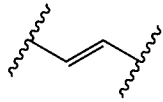 [SMILES: */C=C/*]

which may form a cis, trans, E, or Z double bond.

As used herein, when two substituents on adjacent carbons taken together, along with the two intervening carbon atoms to which they are attached, form a cycloalkyl or a heterocycloalkyl group, or when one substituent and the carbon atom to which it is attached and the carbon atom to which one adjacent substituent is attached, form a cycloalkyl or a heterocycloalkyl group, it is meant that, for example,

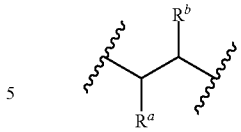

forms a

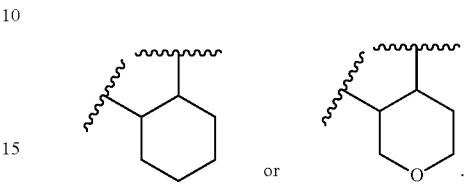

As used herein, when two substituents taken together, along with the carbon atoms to which they are attached and the at least two intervening carbon atoms, form a cycloalkyl or a heterocycloalkyl group, or when one substituent and the carbon atom to which it is attached and the carbon atom to which one non-adjacent substituent is attached, taken together with all intervening carbon atoms, form a cycloalkyl or heterocycloalkyl group, it is meant that, for example,

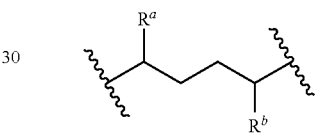

forms a

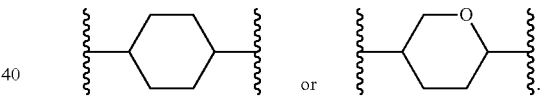

It is understood that, in any compound of this invention having one or more chiral centers, if an absolute stereochemistry is not expressly indicated, then each center may independently be R or S or a mixture thereof. In addition it is understood that, in any compound of this invention having one or more double bond(s) generating geometrical isomers that can be defined as E or Z each double bond may independently be E or Z, or a mixture thereof.

Throughout the present disclosure, when a particular compound comprises a chiral center, the scope of the present disclosure also includes compositions comprising the racemic mixture of the two enantiomers, as well as compositions comprising each enantiomer individually substantially free of the other enantiomer. Thus, for example, contemplated herein is a composition comprising the S enantiomer substantially free of the R enantiomer, or a composition comprising the R enantiomer substantially free of the S enantiomer. By "substantially free" it is meant that the composition comprises less than 10%, or less than 8%, or less than 5%, or less than 3%, or less than 1% of the minor enantiomer. If the particular compound comprises more than one chiral center, the scope of the present disclosure also includes compositions comprising a mixture of the various diastereomers, as well as compositions comprising each diastereomer substantially free of the other diastereomers. The recitation of a compound, without reference to any of its particular diastereomers, includes compositions comprising all four diastereomers, compositions comprising the racemic mixture of R,R and S,S isomers, compositions comprising the racemic mixture of R,S and S,R isomers, compositions comprising the R,R enantiomer substantially free of the other diastereomers, compositions comprising the S,S enantiomer substantially free of the other diastereomers, compositions comprising the R,S enantiomer substantially free of the other diastereomers, and compositions comprising the S,R enantiomer substantially free of the other diastereomers.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methanesulfonates, ethanesulfonates, p-toluenesulfonates and salicylates.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may decrease the rate of metabolic degradation for instance by decreasing O-glucuronidation and or O-sulfation. The prodrug may also have improved solubility in pharmaceutical compositions over the parent drug. An example, without limitation, of a prodrug would be a compound disclosed herein, which is administered as an ester (the "prodrug") to facilitate absorption over a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

In some embodiments of the compound of Formula I, where $R_1$-$R_4$ are optionally substituted, each $R_1$-$R_4$ is independently and optionally substituted with a substituent selected from the group consisting of —CN, halogen, haloalkyl, —O($C_{1-6}$alkyl), —$NR_{31}R_{32}$, —S($C_{1-6}$alkyl), —O($C_{1-6}$haloalkyl).

In some embodiments of the compound of Formula I, where $R_5$-$R_8$ are optionally substituted, each $R_5$-$R_8$ is independently and optionally substituted with a substituent selected from the group consisting of —CN, halogen, haloalkyl, —O($C_{1-6}$alkyl), —$NR_{31}R_{32}$, —S($C_{1-6}$alkyl), —O($C_{1-6}$haloalkyl).

In some embodiments of the compound of Formula I, where $R_{10}$-$R_{16}$ are optionally substituted, each $R_{10}$-$R_{16}$ is independently and optionally substituted with a substituent selected from the group consisting of —CN, halogen, haloalkyl, —O($C_{1-6}$alkyl), —$NR_{31}R_{32}$, —S($C_{1-6}$alkyl), —O($C_{1-6}$haloalkyl).

In some embodiments of the compound of Formula I, X is oxygen.

In some embodiments of the compound of Formula I, $R_1$-$R_4$ are each separately and independently selected from the group consisting of hydrogen, optionally substituted $C_{1-6}$alkyl, optionally substituted $C_{3-6}$cycloalkyl, optionally substituted $C_{1-6}$alkyl($C_{3-6}$cycloalkyl), halogen, optionally substituted $C_{1-6}$haloalkyl, optionally substituted $C_{1-6}$haloalkoxy, —CN, —C(=Z)$R_{30}$, —C(=Z)O$R_{30}$, —C(=Z)$NR_{31}R_{32}$, —C($R_{30}$)=$NR_{31}$, —$NR_{31}R_{32}$, and —N=C$R_{31}R_{32}$.

In some embodiments of the compound of Formula I, $R_1$-$R_4$ are each separately and independently selected from the group consisting of hydrogen, optionally substituted $C_{1-6}$alkyl, optionally substituted $C_{3-6}$cycloalkyl, halogen, optionally substituted $C_{1-6}$haloalkyl, —CN, —C(=Z)$R_{30}$, —C(=Z)O$R_{30}$, —C(=Z)$NR_{31}R_{32}$, and —$NR_{31}R_{32}$.

In some embodiments of the compound of Formula I, $R_1$-$R_4$ are each separately and independently selected from the group consisting of hydrogen, optionally substituted $C_{1-6}$alkyl, optionally substituted $C_{1-6}$haloalkyl, and halogen.

In some embodiments of the compound of Formula I, the halogen is selected from the group consisting of fluoro, chloro, bromo, and iodo.

In some embodiments of the compound of Formula I, $R_1$ is hydrogen or fluoro.

In some embodiments of the compound of Formula I, $R_2$ is hydrogen.

In some embodiments of the compound of Formula I, $R_3$ is hydrogen.

In some embodiments of the compound of Formula I, $R_4$ is hydrogen or fluoro.

In some embodiments of the compound of Formula I, $R_5$-$R_8$ are each separately and independently selected from the group consisting of hydrogen, optionally substituted $C_{1-6}$alkyl, optionally substituted $C_{3-6}$cycloalkyl, optionally substituted $C_{1-6}$alkyl($C_{3-6}$cycloalkyl), halogen, optionally substituted $C_{1-6}$haloalkyl, optionally substituted $C_{1-6}$haloalkoxy, —CN, —C(=Z)$R_{30}$, —C(=Z)O$R_{30}$, —C(=Z)$NR_{31}R_{32}$, —C($R_{30}$)=$NR_{31}$, —$NR_{31}R_{32}$, and —N=C$R_{31}R_{32}$.

In some embodiments of the compound of Formula I, $R_5$-$R_8$ are each separately and independently selected from the group consisting of hydrogen, optionally substituted $C_{1-6}$alkyl, optionally substituted $C_{3-6}$cycloalkyl, halogen, optionally substituted $C_{1-6}$haloalkyl, —CN, —C(=Z)$R_{30}$, —C(=Z)O$R_{30}$, —C(=Z)$NR_{31}R_{32}$, and —$NR_{31}R_{32}$.

In some embodiments of the compound of Formula I, $R_5$-$R_8$ are each separately and independently selected from the group consisting of hydrogen, optionally substituted $C_{1-6}$alkyl, optionally substituted $C_{1-6}$haloalkyl, and halogen.

In some embodiments of the compound of Formula I, $R_5$-$R_8$ are each hydrogen.

In some embodiments of the compound of Formula I, $R_{10}$-$R_{16}$ are each separately and independently selected from the group consisting of hydrogen, optionally substituted $C_{1-6}$alkyl, optionally substituted $C_{3-6}$cycloalkyl, optionally substituted $C_{1-6}$alkyl($C_{3-6}$cycloalkyl), halogen, optionally substituted $C_{1-6}$haloalkyl, optionally substituted $C_{1-6}$haloalkoxy, —CN, —C(=Z)$R_{30}$, —C(=Z)O$R_{30}$, —C(=Z)$NR_{31}R_{32}$, —C($R_{30}$)=$NR_{31}$, —$NR_{31}R_{32}$, and —N=C$R_{31}R_{32}$.

In some embodiments of the compound of Formula I, $R_{10}$-$R_{16}$ are each separately and independently selected from the group consisting of hydrogen, optionally substituted $C_{1-6}$alkyl, optionally substituted $C_{3-6}$cycloalkyl, halogen, optionally substituted $C_{1-6}$haloalkyl, —CN, —C(=Z)$R_{30}$, —C(=Z)O$R_{30}$, —C(=Z)$NR_{31}R_{32}$, and —$NR_{31}R_{32}$.

In some embodiments of the compound of Formula I, $R_{10}$-$R_{16}$ are each separately and independently selected from the group consisting of hydrogen, optionally substituted $C_{1-6}$alkyl, optionally substituted $C_{1-6}$haloalkyl, and halogen.

In some embodiments of the compound of Formula I, two $R_{10}$-$R_{16}$ on adjacent carbons taken together, along with the two intervening carbon atoms to which they are attached, form a double bond.

In some embodiments of the compound of Formula I, $R_{10}$ and $R_{11}$ taken together, along with the two intervening carbon atoms to which they are attached, form a double bond;

In some embodiments of the compound of Formula I, $R_{20}$ is selected from the group consisting of hydrogen, optionally substituted alkyl, optionally substituted cycloalkyl, optionally substituted aryl, optionally substituted heteroaryl, optionally substituted heteroalicyclyl, and haloalkyl.

In some embodiments of the compound of Formula I, the alkyl is selected from the group consisting of methyl, ethyl, isopropyl, sec-propyl, butyl, isobutyl, and tert-butyl.

In some embodiments of the compound of Formula I, $R_{20}$ is selected from the group consisting of hydrogen and optionally substituted alkyl.

In some embodiments of the compound of Formula I, $R_{20}$ is hydrogen.

In some embodiments of the compound of Formula I, n is 2, while in other embodiments of the compound of Formula I, n is 3.

In some embodiments, at least one atom in the compound is a radioisotope. The radioisotope may be an isotope of hydrogen, carbon, oxygen, nitrogen, or halogen. Those of skill in the art recognize an isotope of hydrogen, i.e., tritium ($^3H$), certain isotopes of carbon, e.g., $^{11}C$, certain isotopes of iodine, e.g., $^{123}I$, certain isotopes of fluorine, e.g., $^{18}F$, certain isotopes of nitrogen, e.g., $^{13}N$, and certain isotopes of oxygen, e.g., $^{15}O$, are radioactive and once incorporated into a compound, their presence can be detected using known methods in the art, for example positron emission tomography (PET) or photon emission computed tomography (SPECT).

The present disclosure also embraces isotopically-labeled compounds disclosed herein, which are identical to the compounds of Formula I or Formula II, but for the fact that one or more atoms are replaced by an atom having an atomic mass or mass number different from the atomic mass or mass number of the most abundant isotope found in nature. Examples of isotopes that can be incorporated into compounds of Formula I or Formula II include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$, and $^{36}Cl$, respectively.

Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

In another aspect, disclosed herein is a compound selected from the group consisting of

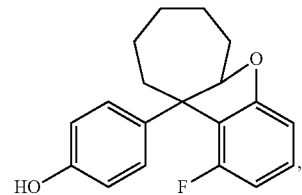,

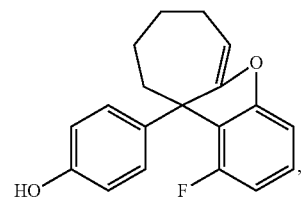,

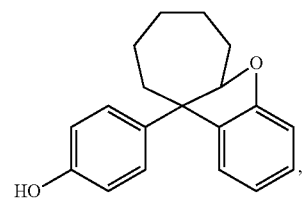,

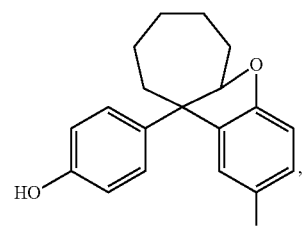,

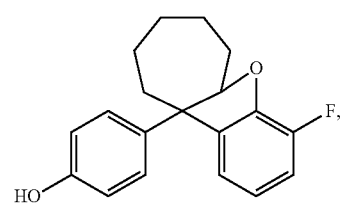,

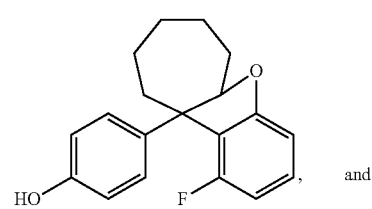, and

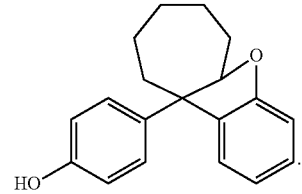.

In another aspect, disclosed herein is a compound selected from the group consisting of
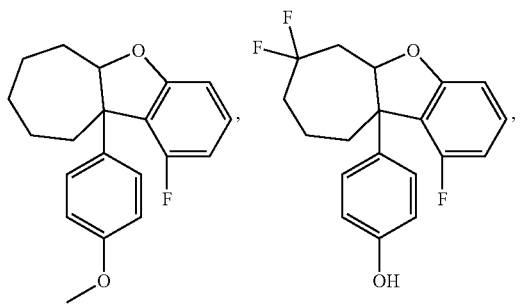
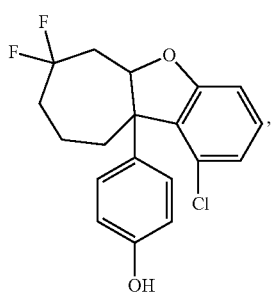
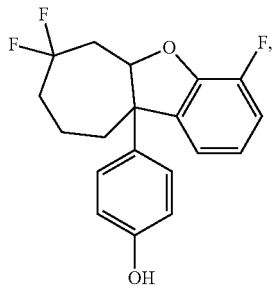
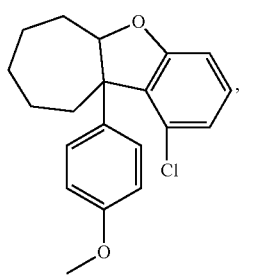
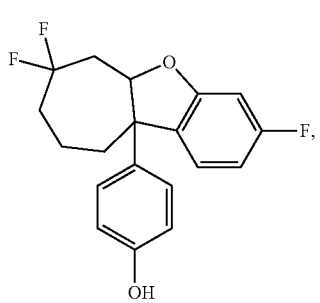
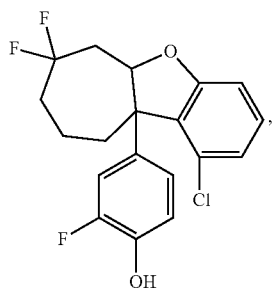
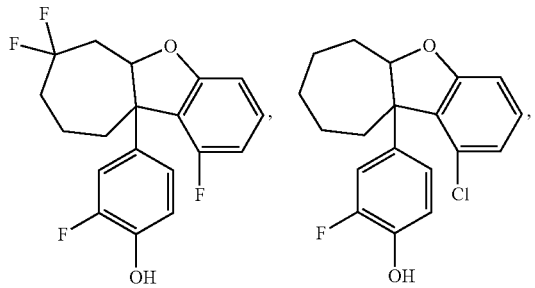
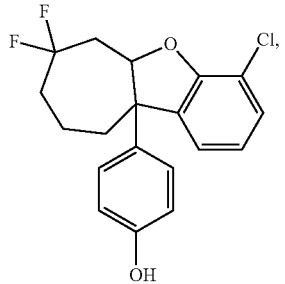
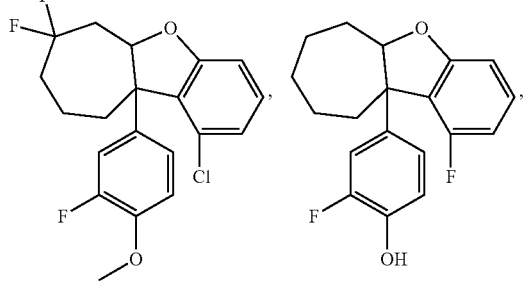
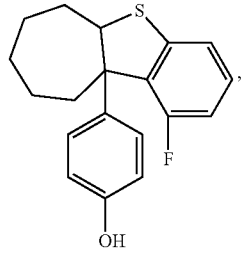
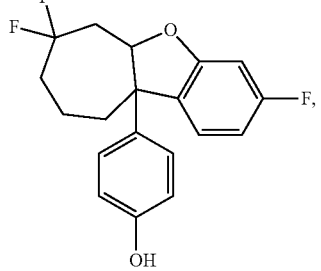

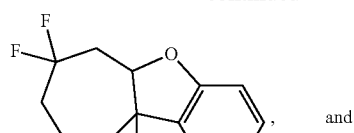
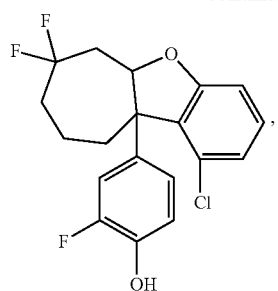 and
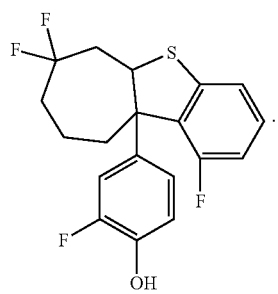
In another aspect, disclosed herein is a compound selected from the group consisting of
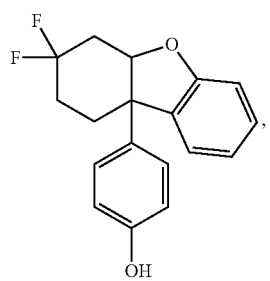
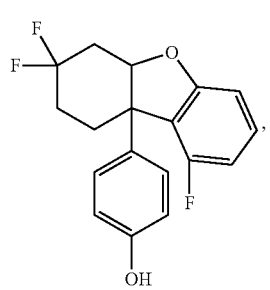
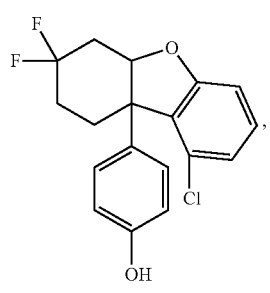
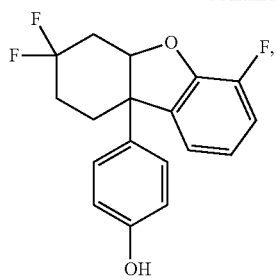
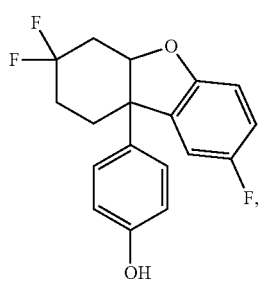
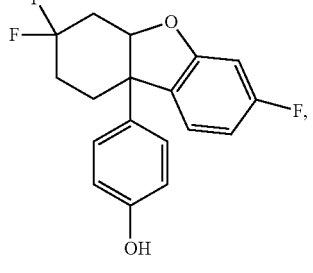
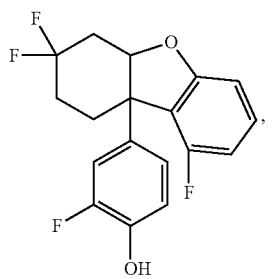
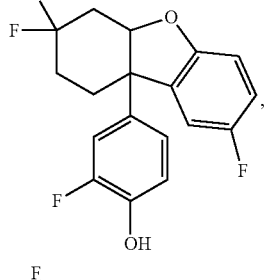
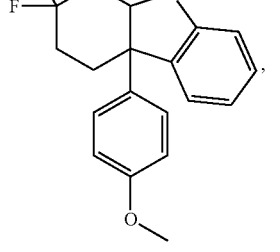

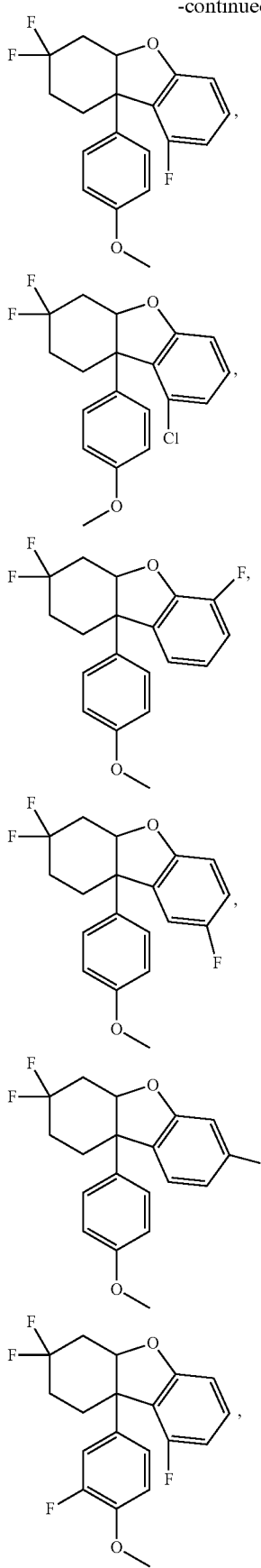

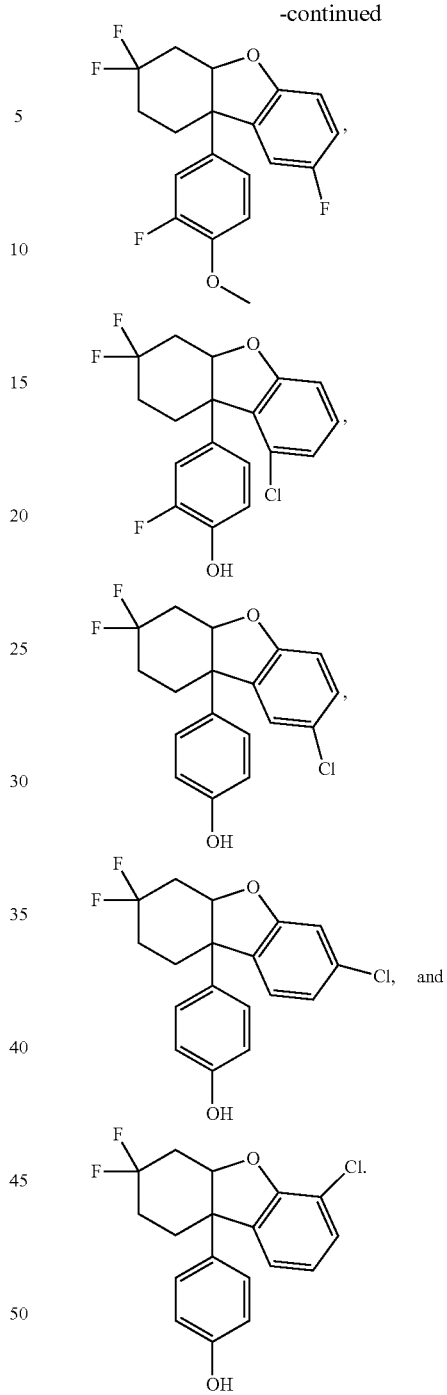

General synthetic routes to the compounds of this invention are shown in Schemes 1, 1a-1f, 2, 2a-2b, and 3. The routes shown are illustrative only and are not intended, nor are they to be construed, to limit the scope of this invention in any manner whatsoever. Those skilled in the art will be able to recognize modifications of the disclosed synthesis and to devise alternate routes based on the disclosures herein; all such modifications and alternate routes are within the scope of this invention. For example, compounds of this invention can be obtained according to the method depicted in Schemes 1. In these schemes, $R_1$ can be any of $R_1$-$R_4$ of the compounds of Formula I; $R_2$ can be any of $R_5$-$R_6$ of the compounds of Formula I; $R_3$ can be any of $R_{10}$-$R_{16}$ of the compounds of Formula I; and R is $R_{20}$ of the compounds of Formula I.

Scheme 1

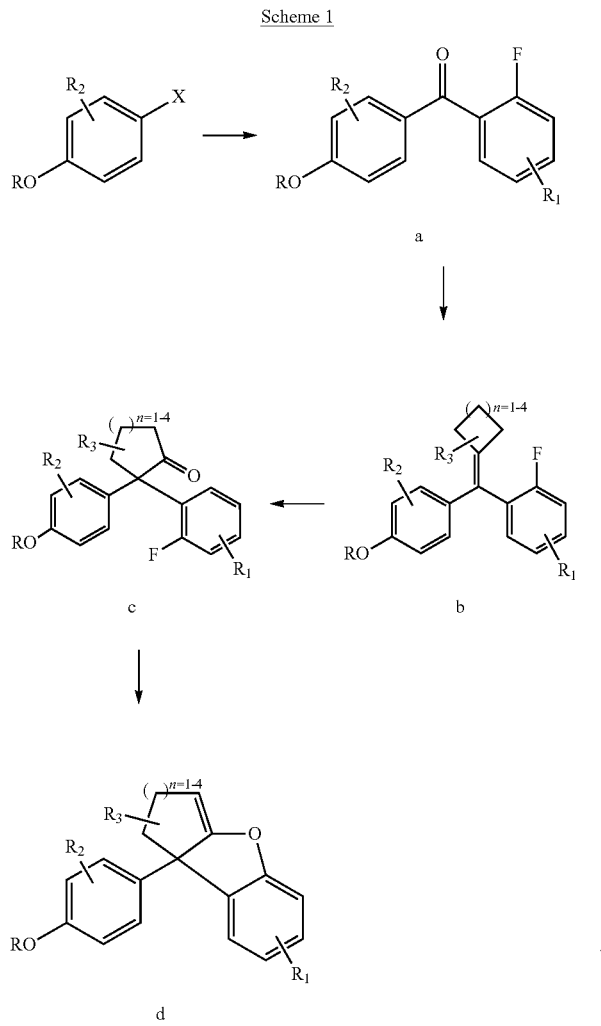

Compounds of this invention can be synthesized via multiple steps from benzophenone derivatives (Scheme 1, compounds a). Benzophenones can for example be synthesized from various benzoic acid derivatives as described in the literature and are well-known to those skilled in the art. However, it is also possible to synthesize benzophenones from benzoyl chlorides as depicted in schemes 1a-1b.

Scheme 1a

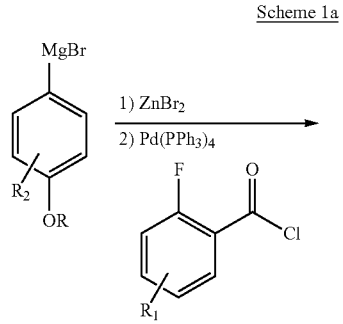

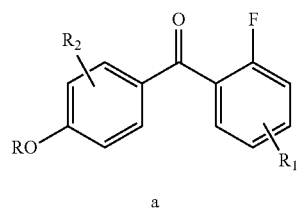

Scheme 1b

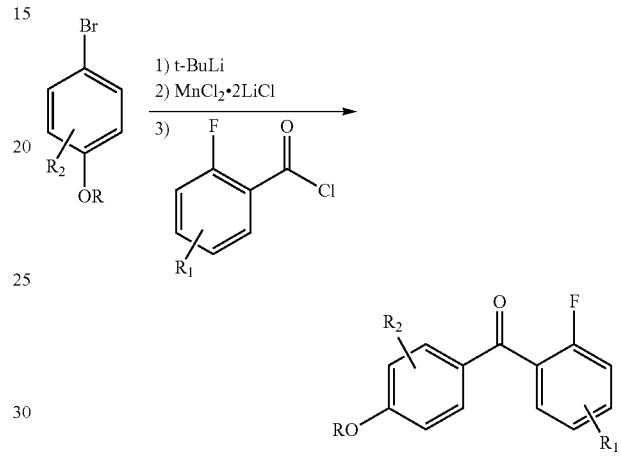

The next step in the synthesis of compounds of this invention is to transform the obtained benzophenones into alkenes (Scheme 1, compounds b). This can for example be done by a McMurry type reaction using cyclic ketones, $TiCl_4$ and Zn as depicted in Scheme 1c.

Scheme 1c

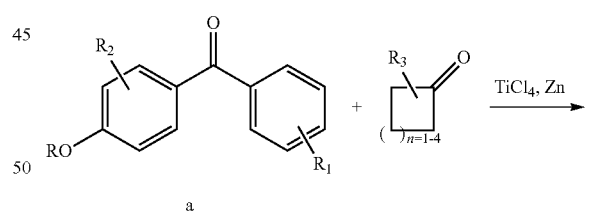

Alternatively, the alkene intermediates (Scheme 1, compounds b) can be obtained from a Cerium Grignard reaction as depicted in Scheme 1d.

Scheme 1d

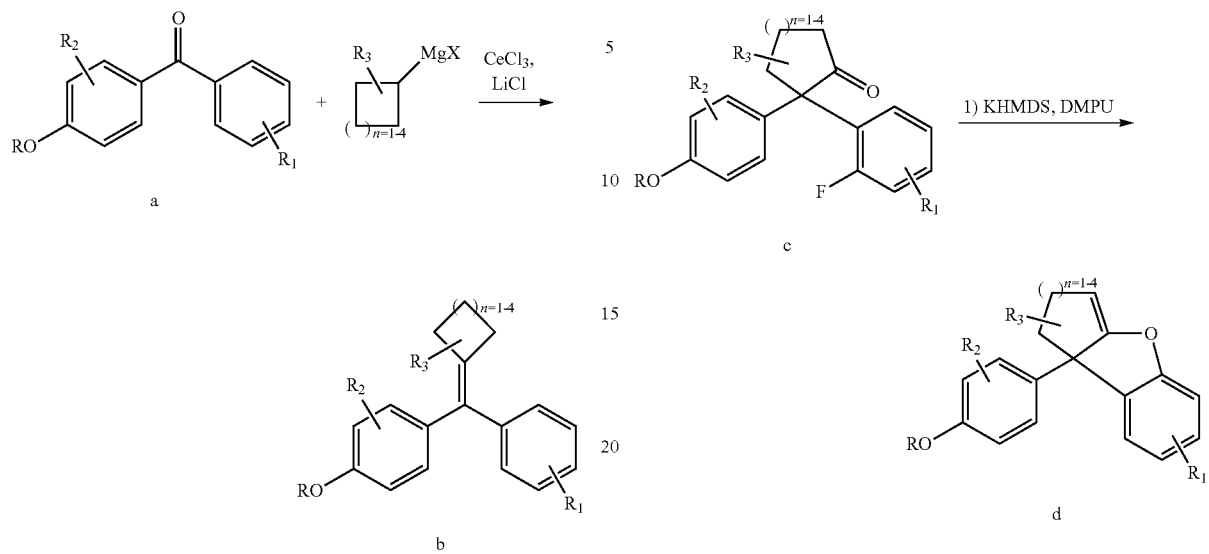

The next step in the synthesis of compounds of this invention is to transform the obtained alkenes into cyclic ketones (Scheme 1, compounds c). This can for example be done by a two-step procedure by use of mCPBA and TFA as depicted in Scheme 1e.

Scheme 1e

The next step in the synthesis of compounds of this invention is to perform a ring closing procedure of the obtained cyclic ketones yielding compounds of this invention (Scheme 1, compounds d). This can be done through treatment of the ketone with a base, for example Potassium-Hexamethyldisilazane (KHMDS) as depicted in Scheme 1f.

Alternatively, compounds of this invention can be obtained according to the method depicted in Scheme 2 where compounds a-c are obtained by the procedures described in scheme 1a-1e.

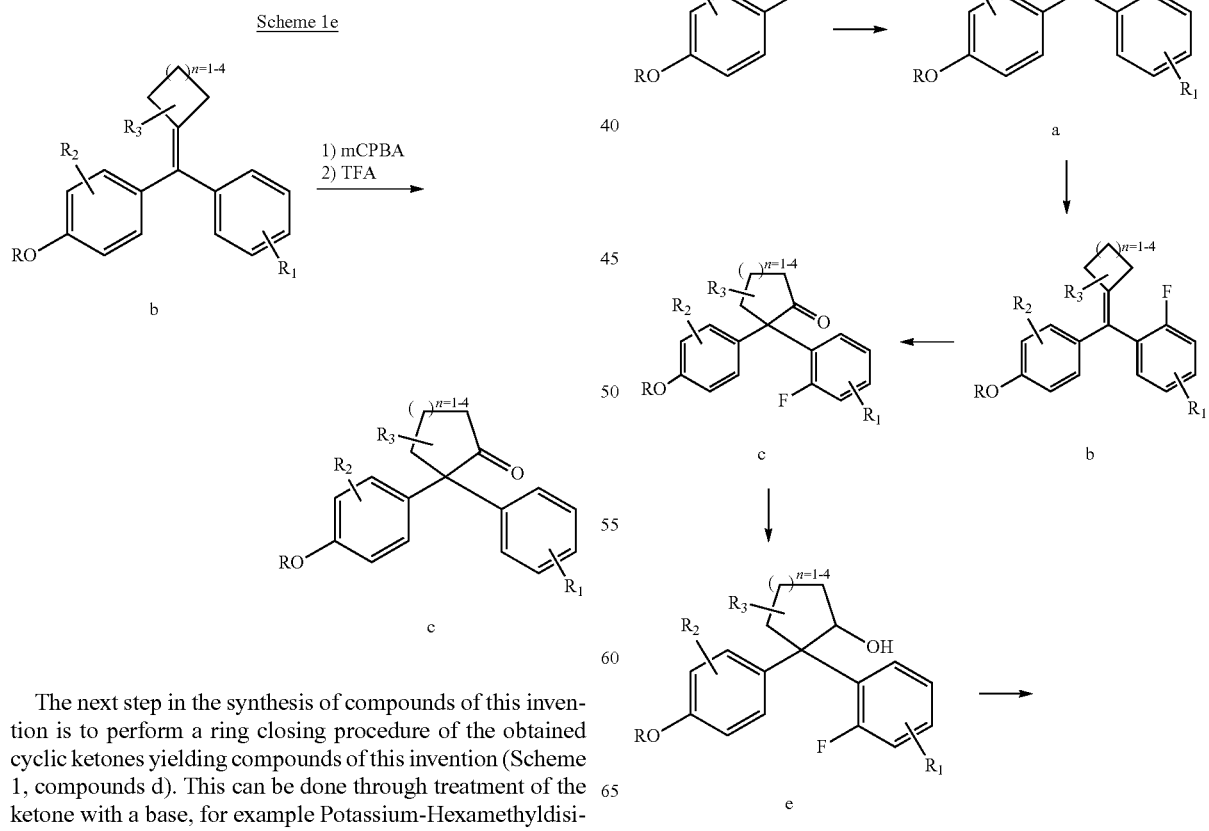

-continued

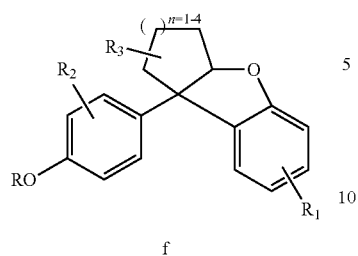

f

The next step in the synthesis of compounds of this invention is to transform the cyclic ketones (Scheme 2, compounds c) into the corresponding alcohol (Scheme 2, compounds e). The reduction can be performed by using methods described in the literature. For example lithium aluminum hydride (LiAlH$_4$) can be used as reducing agent as depicted in Scheme 2a.

The next step in the synthesis of compounds of this invention is to ring close the alcohol (Scheme 2, compounds e) by a substitution step yielding compounds of this invention (Scheme 2, compounds f). The ring closure can for example be performed by using potassium tert-butoxide (tBuOK) as base, as depicted in Scheme 2b.

Scheme 2b

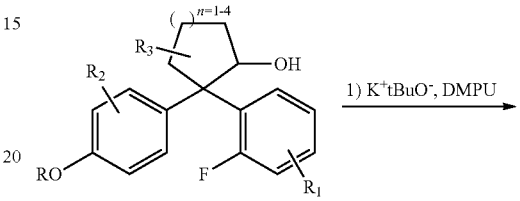

Scheme 2a

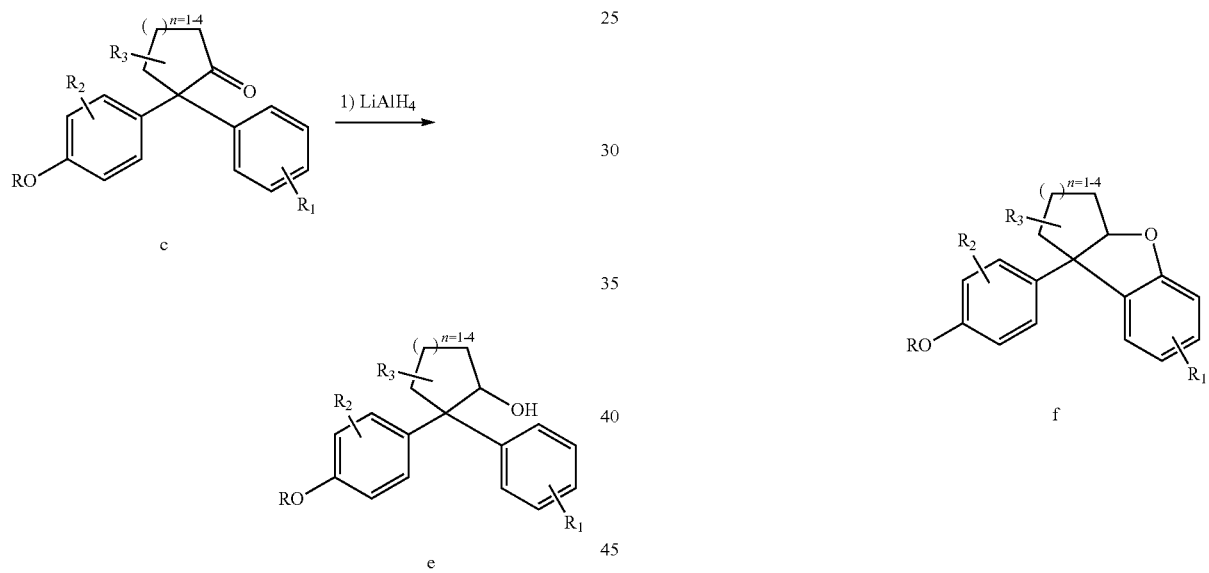

Some of the other compounds disclosed herein are synthesized by the procedure depicted in Scheme 3.

Scheme 3

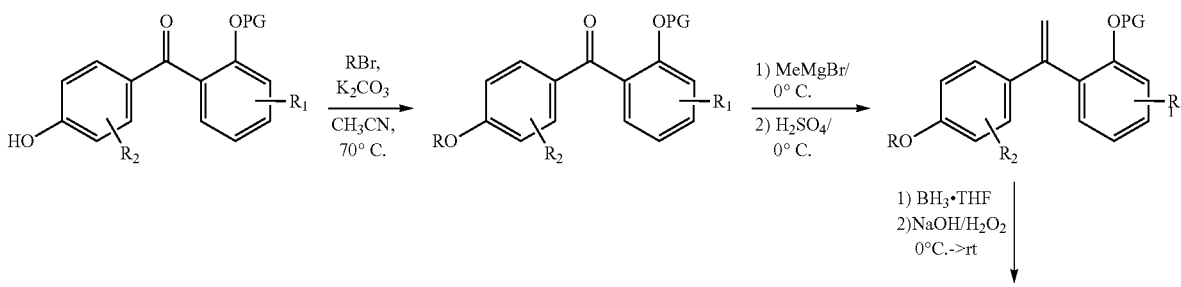

-continued

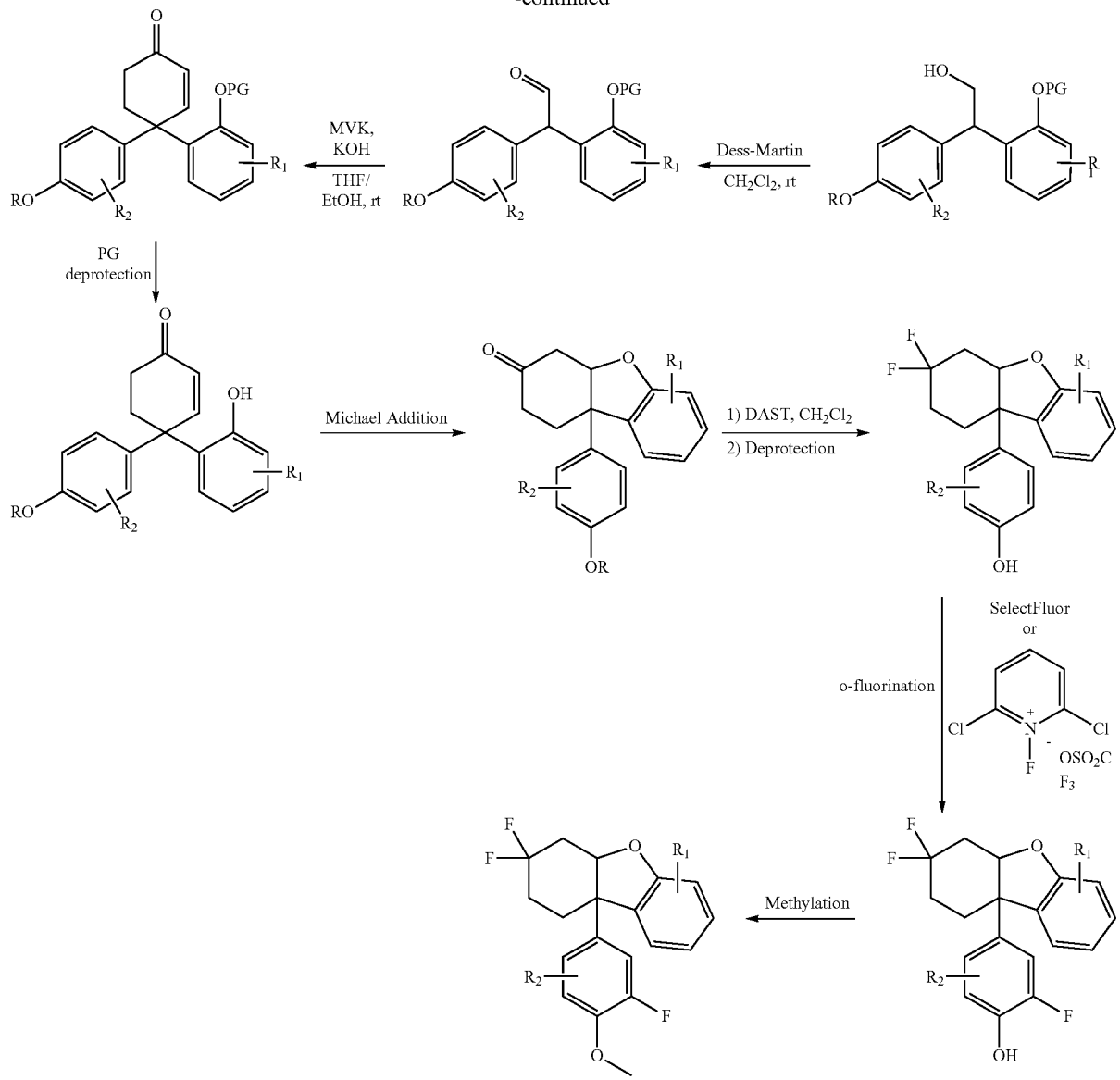

PG = Protection Group
as example, benzyl and p-methoxy benzyl

In another aspect, disclosed herein are pharmaceutical compositions comprising one or more compounds of Formula I as described above, and a physiologically acceptable carrier, diluent, or excipient, or a combination thereof.

The term "pharmaceutical composition" refers to a mixture of one or more compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990, which is hereby incorporated by reference in its entirety.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, intraocular injections or as an aerosol inhalant.

Alternately, one may administer the compound in a local rather than systemic manner, for example, via injection of the compound directly into the area of pain or inflammation, often in a depot or sustained release formulation. Furthermore, one may administer the drug in a targeted-drug-delivery system, for example, in a liposome coated with a tissue-specific antibody. The liposomes will be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes.

Pharmaceutical compositions for use in accordance with the present disclosure may be formulated in a conventional manner using one or more physiologically acceptable carriers comprising excipients and auxiliaries, which facilitate processing of the active compounds into preparations, which can be used pharmaceutically. Proper formulation is dependent upon the route of administration chosen. Any of the well-known techniques, carriers, and excipients may be used as suitable and as understood in the art; e.g., as disclosed in Remington's Pharmaceutical Sciences, cited above.

For injection, the agents disclosed herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination disclosed herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds disclosed herein is a co-solvent system comprising benzyl alcohol, a nonpolar surfactant, a water-miscible organic polymer, and an aqueous phase. A common co-solvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; and other biocompatible polymers may replace polyethylene glycol, e.g., polyvinyl pyrrolidone. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations disclosed herein may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acids or base forms.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", Chapter 1, which is hereby incorporated by reference in its entirety). Typically, the dose range of the composition administered to the patient can be from about 0.5 to 1000 mg/kg of the patient's body weight, or 1 to 500 mg/kg, or 10 to 500 mg/kg, or 50 to 100 mg/kg of the patient's body weight. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising one or more compounds disclosed herein formulated in a compatible pharmaceutical carrier may also be prepared, placed in an appropriate container, and labeled for treatment of an indicated condition.

Also disclosed herein are methods of treating clinical manifestations in which modulation of the activity of the estrogen receptor function is beneficial, comprising identifying a subject in need thereof and administering to the subject, or contacting the subject with, a therapeutically effective amount of one or more compounds of Formula I.

Also disclosed herein are methods of treating or preventing inflammatory bowel syndrome, Crohn's disease, ulcerative proctitis or colitis comprising identifying a subject in need thereof and administering to the subject, or contacting the subject with, a therapeutically effective amount of one or more compounds of Formula I.

Also disclosed herein are methods of treating or preventing prostatic hypertrophy, uterine leiomyomnas, breast carcinoma, endometrial carcinoma, polycystic ovary syndrome, endometrial polyps, benign breast disease, adenomyosis, ovarian carcinoma, melanoma, prostate carcinoma, colon carcinoma, or brain tumors including glioblastoma, astrocytoma, glioma, or meningioma comprising identifying a subject in need thereof and administering to the subject, or contacting the subject with, a therapeutically effective amount of one or more compounds of Formula I.

Also disclosed herein are methods of treating or preventing prostatitis or interstitial cystitis comprising identifying a subject in need thereof and administering to the subject, or contacting the subject with, a therapeutically effective amount of one or more compounds of Formula I.

Also disclosed herein are methods of hormonal replacement therapy comprising identifying a subject in need thereof and administering to the subject, or contacting the subject with, a therapeutically effective amount of one or more compounds of Formula I.

Also disclosed herein are methods of treating or preventing bone density loss including osteoporosis and osteopenia comprising identifying a subject in need thereof and administering to the subject, or contacting the subject with, a therapeutically effective amount of one or more compounds of Formula I.

Also disclosed herein are methods of lowering cholesterol, triglycerides, or LDL levels comprising identifying a subject in need thereof and administering to the subject, or contacting the subject with, a therapeutically effective amount of a compound of Formula I, comprising identifying a subject in need thereof and administering to the subject, or contacting the subject with, a therapeutically effective amount of one or more compounds of Formula I.

Also disclosed herein are methods of treating or preventing discholesterolemia or dislipidemia comprising identifying a subject in need thereof and administering to the subject, or contacting the subject with, a therapeutically effective amount of one or more compounds of Formula I.

Also disclosed herein are methods of treating or preventing cardiovascular disease, atherosclerosis, hypertension, peripheral vascular disease, restenosis or vasospasm comprising identifying a subject in need thereof and administering to the subject, or contacting the subject with, a therapeutically effective amount of one or more compounds of Formula I.

Also disclosed herein are methods of treating impaired cognition or providing neuroprotection comprising identifying a subject in need thereof and administering to the subject, or contacting the subject with, a therapeutically effective amount of one or more compounds of Formula I.

Also disclosed herein are methods of treating or preventing neurodegenerative disorders, including Alzheimer's disease, Huntington's disease, Parkinson's disease or other dementias comprising identifying a subject in need thereof and administering to the subject, or contacting the subject with, a therapeutically effective amount of one or more compounds of Formula I.

Also disclosed herein are methods of treating a spinal cord injury comprising identifying a subject in need thereof and administering to the subject, or contacting the subject with, a therapeutically effective amount of one or more compounds of Formula I.

Also disclosed herein are methods of treating or preventing cognitive decline, stroke, or anxiety comprising identifying a subject in need thereof and administering to the subject, or contacting the subject with, a therapeutically effective amount of one or more compounds of Formula I.

Also disclosed herein are methods of treating or preventing free radical induced disease states comprising identifying a subject in need thereof and administering to the subject, or contacting the subject with, a therapeutically effective amount of one or more compounds of Formula I.

Also disclosed herein are methods of treating or preventing vaginal atrophy, vulvar atrophy, atrophic vaginitis, vaginal dryness, pruritus, dyspareunia, frequent urination, urinary incontinence, or urinary tract infections comprising identifying a subject in need thereof and administering to the subject, or contacting the subject with, a therapeutically effective amount of one or more compounds of Formula I.

Also disclosed herein are methods of treating or preventing vasomotor symptoms including flushing or hot flashes comprising identifying a subject in need thereof and administering to the subject, or contacting the subject with, a therapeutically effective amount of one or more compounds of Formula I.

Also disclosed herein are methods of preventing conception comprising identifying a subject in need thereof and administering to the subject, or contacting the subject with, a therapeutically effective amount of one or more compounds of Formula I.

Also disclosed herein are methods of treating or preventing endometriosis comprising identifying a subject in need thereof and administering to the subject, or contacting the subject with, a therapeutically effective amount of one or more compounds of Formula I.

Also disclosed herein are methods of treating or preventing arthritis, including but not limited to rheumatoid arthritis, osteoarthritis, arthropathies, or arthropathiesendometriosis comprising identifying a subject in need thereof and administering to the subject, or contacting the subject with, a therapeutically effective amount of one or more compounds of Formula I.

Also disclosed herein are methods of treating or preventing psoriasis or dermatitis comprising identifying a subject in need thereof and administering to the subject, or contacting the subject with, a therapeutically effective amount of one or more compounds of Formula I.

Also disclosed herein are methods of treating or preventing asthma or pleurisy comprising identifying a subject in need thereof and administering to the subject, or contacting the subject with, a therapeutically effective amount of one or more compounds of Formula I.

Also disclosed herein are methods of treating or preventing multiple sclerosis, systemic lupus erthematosis, uveitis, sepsis, or hemmorhagic shock comprising identifying a subject in need thereof and administering to the subject, or contacting the subject with, a therapeutically effective amount of one or more compounds of Formula I.

Also disclosed herein are methods of treating or preventing type II diabetes comprising identifying a subject in need thereof and administering to the subject, or contacting the subject with, a therapeutically effective amount of one or more compounds of Formula I.

Also disclosed herein are methods for treating acute and chronic inflammation of any type comprising identifying a subject in need thereof and administering to the subject, or contacting the subject with, a therapeutically effective amount of one or more compounds of Formula I.

Also disclosed herein are methods of treating or preventing lung disorders such as asthma, chronic obstructive pulmonary disease comprising identifying a subject in need thereof and administering to the subject, or contacting the subject with, a therapeutically effective amount of one or more compounds of Formula I.

Also disclosed herein are methods of treating or preventing acute or chronic pain, including neuropathic pain comprising identifying a subject in need thereof and administering to the subject, or contacting the subject with, a therapeutically effective amount of one or more compounds of Formula I.

Also disclosed herein are methods of treating or preventing ophthalmologic disorders including but not limited to glaucoma, dry eye, macular degeneration comprising identifying a subject in need thereof and administering to the subject, or contacting the subject with, a therapeutically effective amount of one or more compounds of Formula I.

Also disclosed herein are methods of modulating or specifically agonizing one or more Estrogen receptors where the methods comprise identifying a subject in need of treatment or prevention and administering to the subject, or contacting the subject with, a pharmaceutically effective amount of one or more compounds of Formula I.

Also disclosed herein are methods of reducing inflammation, treating neuropathic pain, treating allergic conjunctivitis, reducing IL-4 levels, decreasing IFN-γ levels, treating dry eye, or increasing IL-12 levels in a subject comprising identifying a subject in need of the reducing inflammation, treating neuropathic pain, treating allergic conjunctivitis, reducing IL-4 levels, decreasing IFN-γ levels, treating dry eye, or increasing IL-12 levels; and administering to the subject, or contacting the subject with, a pharmaceutically effective amount of an estrogen receptor β (ERβ) agonist, wherein the ERβ agonist is one or more compounds of Formula I.

In some embodiments, the inflammation is in the eye. In some of these embodiments, the inflammation results in lid edema, hyperemia, chemosis, or tearing. In other embodiments, the inflammation is due to an ophthalmologic disorder selected from the group consisting of uveitis, blepharitis, meibonian gland disease, glaucoma, dry eye, or macular degeneration, or is an ocular manifestation of a systemic inflammatory disease selected from Sjogrens Syndrome, ocular sicatricial pemphygoid and Lupus erythmatosis.

In other embodiments, the inflammation is in the gastrointestinal tract.

In some embodiments, the inflammation is acute or chronic inflammation.

In certain embodiments, the inflammation is due to arthritis.

In certain embodiments, the ERβ agonist is a selective ERβ agonist.

In some embodiments, the ERβ agonist is administered topically, whereas in other embodiments, the ERβ agonist is administered intraperitoneally, and in yet other embodiments, the ERβ agonist is administered orally. In further embodiments, the ERβ agonist is administered systemically.

In some embodiments, the neuropathic pain is hyperalgesia, which can be tactile hyperalgesia. In other embodiments, the neuropathic pain is allodynia. In further embodiments, the neuropathic pain is selected from the group of phantom limb pain, postherpetic neuralgia, reflex sympathetic dystrophy, causalgia, complex regional pain syndrome II, painful HIV-associated neuropathy, and diabetic neuropathy. In additional embodiments, the neuropathic pain is associated with a medical condition selected from the group of traumatic nerve injury, multiple sclerosis, stroke, syringomyelia, epilepsy, spinal cord injury, and cancer.

Another embodiment is a method of identifying a compound that alleviates inflammation in a subject, comprising identifying a subject suffering from inflammation; administering to the subject, or contacting the subject with, at least one compound of Formula I, as defined herein; and determining if the at least one compound reduces inflammation in the subject.

Also disclosed herein is a method of reducing inflammation in a subject comprising identifying a subject in need of the reduction in inflammation; and administering to the subject, or contacting the subject with, a pharmaceutically effective amount of an ERβ agonist.

In some embodiments, the inflammation to be treated is in the eye. In some of these embodiments, the inflammation results in lid edema, hyperemia, chemosis, or tearing. In other embodiments, inflammation is due to an ophthalmologic disorder selected from the group consisting of uveitis, blepharitis, meibonian gland disease, glaucoma, dry eye, or macular degeneration, or is an ocular manifestation of a systemic inflammatory disease such as Sjogrens Syndrome, ocular sicatricial pemphygoid and Lupus erythmatosis.

In some embodiments, the inflammation is in the gastrointestinal tract. In some of these embodiments, the inflammation is colitis, or is caused by colitis.

In other embodiments, the inflammation is due to arthritis.

In some embodiments, the inflammation is acute, whereas in other embodiments, the inflammation is chronic.

Also disclosed herein is a method of treating allergic conjunctivitis in a subject comprising identifying a subject in need of such treatment; and administering to the subject, or contacting the subject with, a pharmaceutically effective amount of an ERβ agonist.

Also disclosed herein is a method of reducing IL-4 levels in a subject, comprising identifying a subject in need of reduction in IL-4 levels; and administering to the subject, or contacting the subject with, a pharmaceutically effective amount of an ERβ agonist.

Also disclosed herein is a method of reducing IFN-γ levels in a subject, comprising identifying a subject in need of reduction in IFN-γ levels; and administering to the subject, or contacting the subject with, a pharmaceutically effective amount of an ERβ agonist.

Also disclosed herein is a method of treating neuropathic pain in a subject, comprising identifying a subject in need of the treatment of neuropathic pain; and administering to the subject, or contacting the subject with, a pharmaceutically effective amount of an ERβ agonist.

Neuropathic pain is caused by abnormalities in the nerves, spinal cord, or brain and includes, without limitation, phantom limb pain, postherpetic neuralgia, reflex sympathetic dystrophy, causalgia, complex regional pain syndrome II, painful HIV-associated neuropathy, diabetic neuropathy. Neuropathic pain is also associated with many medical conditions including, without limitation, traumatic nerve injury, multiple sclerosis, stroke, syringomyelia, epilepsy, spinal cord injury, and cancer. The methods disclosed herein are useful in the treatment of all of the aforementioned manifestations of neuropathic pain.

In some embodiments, the neuropathic pain is mechanical hyperalgesia. In other embodiments, the neuropathic pain is allydonia.

Also disclosed herein is a method of treating or preventing cancer in a subject, comprising identifying a subject in need thereof; and administering to the subject, or contacting the subject with, a pharmaceutically effective amount of one or more compounds of Formula I, where the cancer is selected from the group consisting of colorectal cancer, prostate cancer, breast cancer, ovarian cancer, endometrial cancer, and uterine cancer.

In some embodiments, in the above methods, the compound of Formula I is a compound selected from the group consisting of:
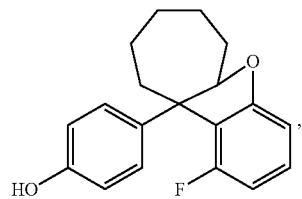
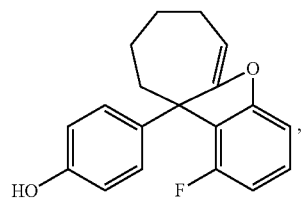
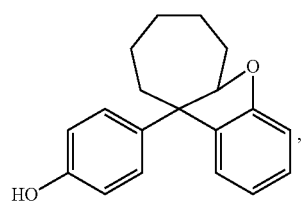
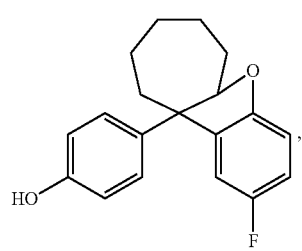
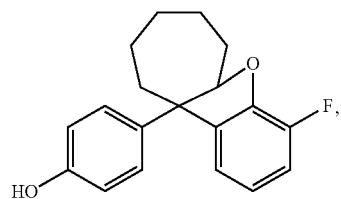
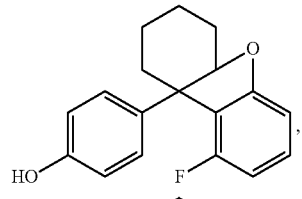
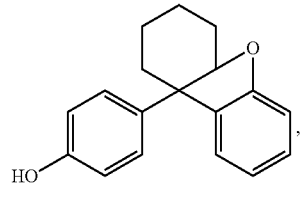
-continued
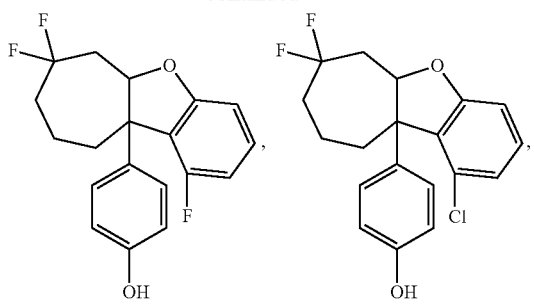
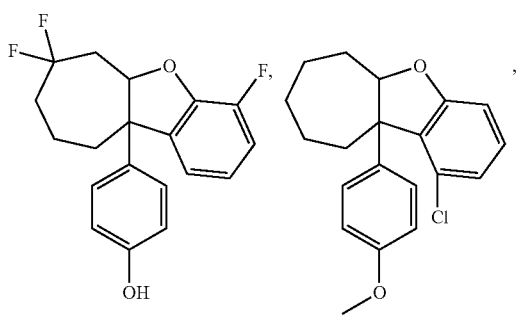
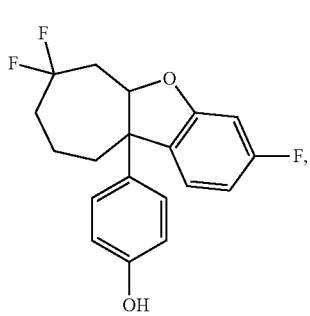
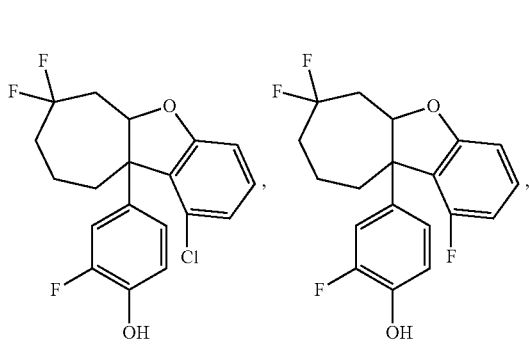
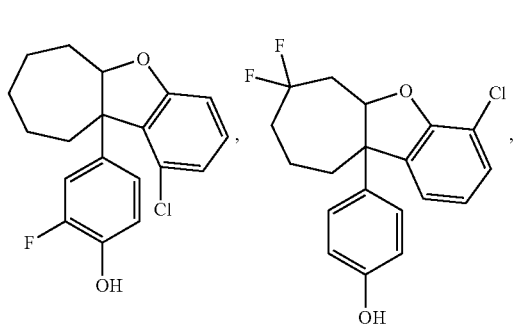

41
-continued
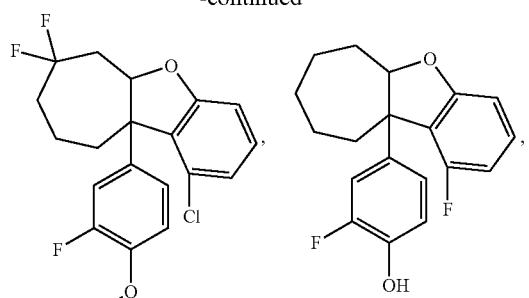
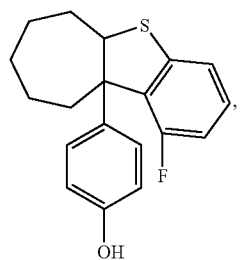
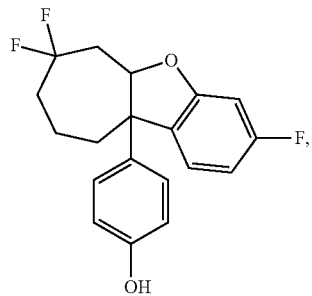
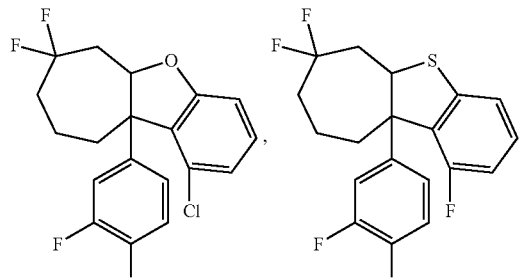
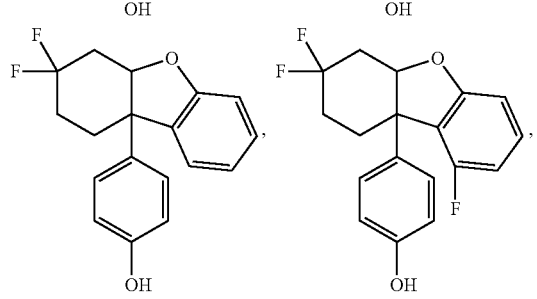
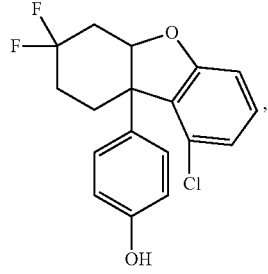
42
-continued
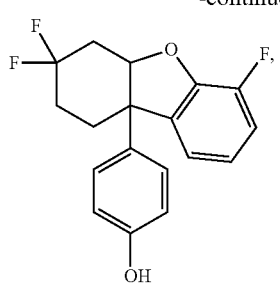
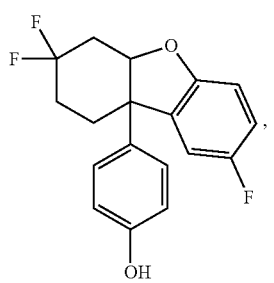
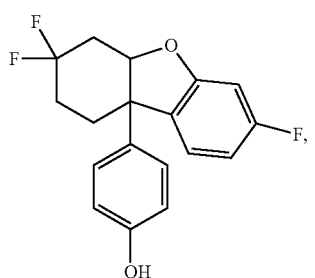
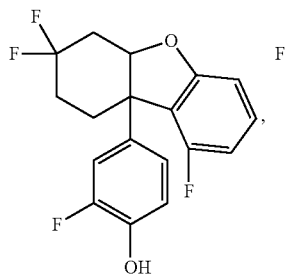
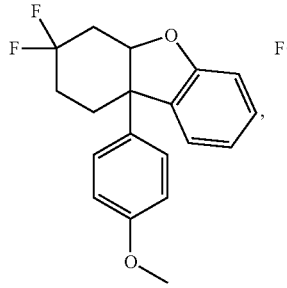
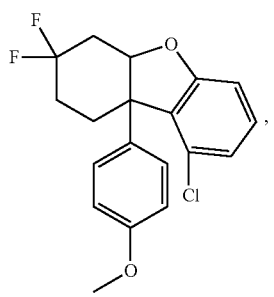

-continued

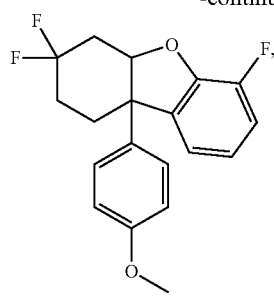

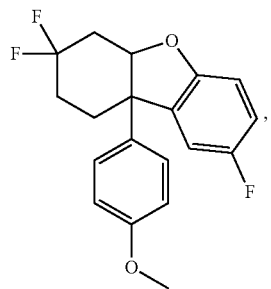

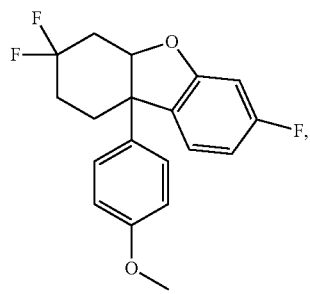

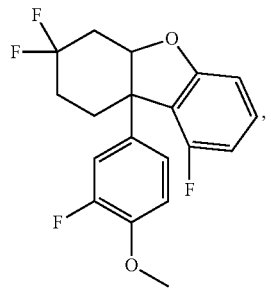

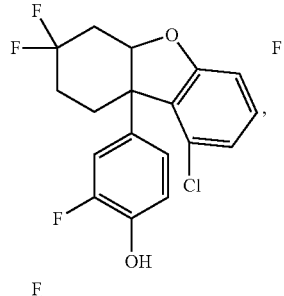

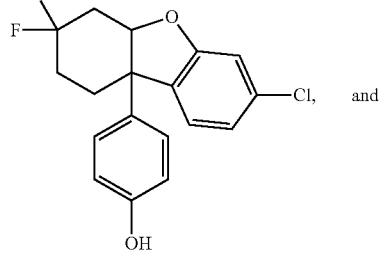

-continued

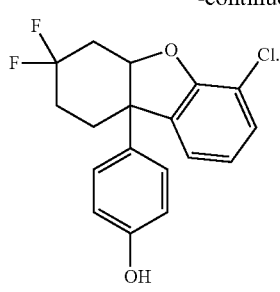

Also disclosed herein is a method of increasing IL-12 levels in a subject, comprising identifying a subject in need of increase in IL-12 levels; and administering to the subject, or contacting the subject with, a pharmaceutically effective amount of an ERβ agonist.

In some embodiments, the ERβ agonist is a compound of Formula I, as described herein. In some of these embodiments, the compound of Formula I is selected from the group consisting of

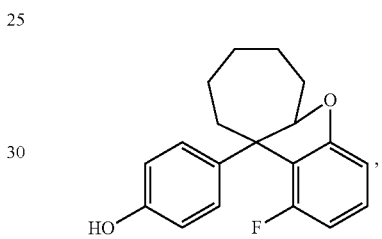

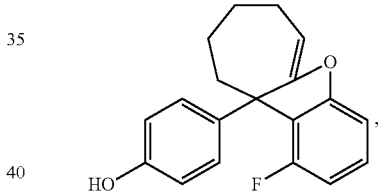

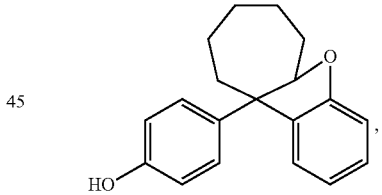

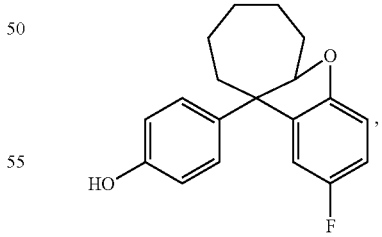

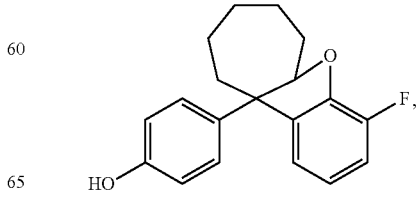

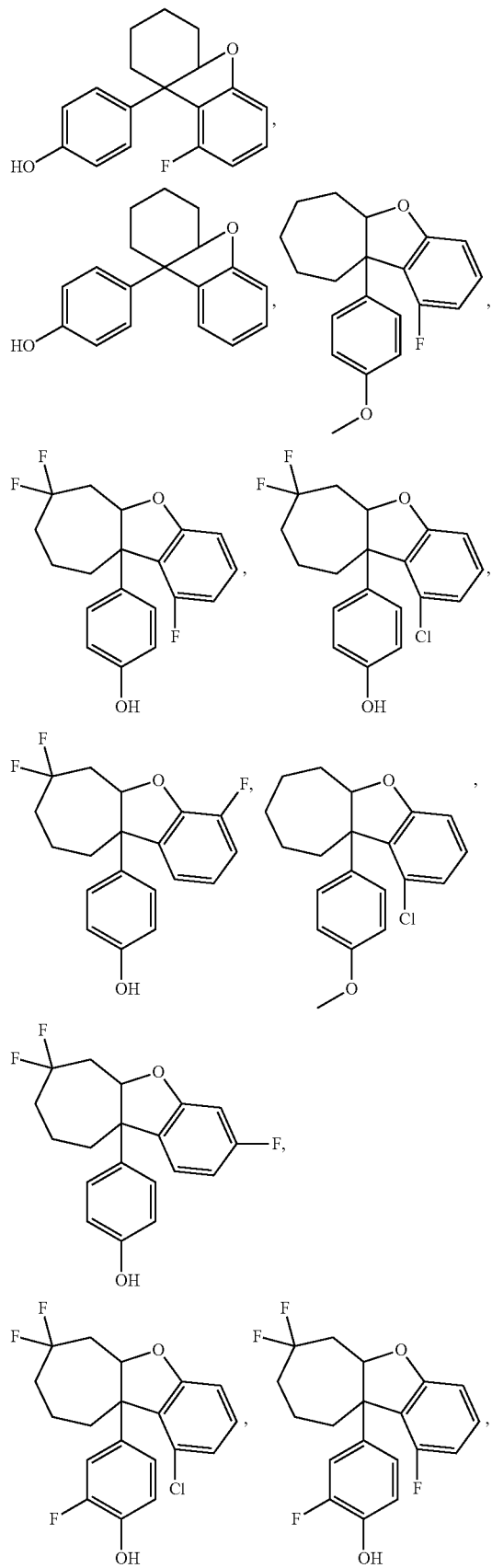
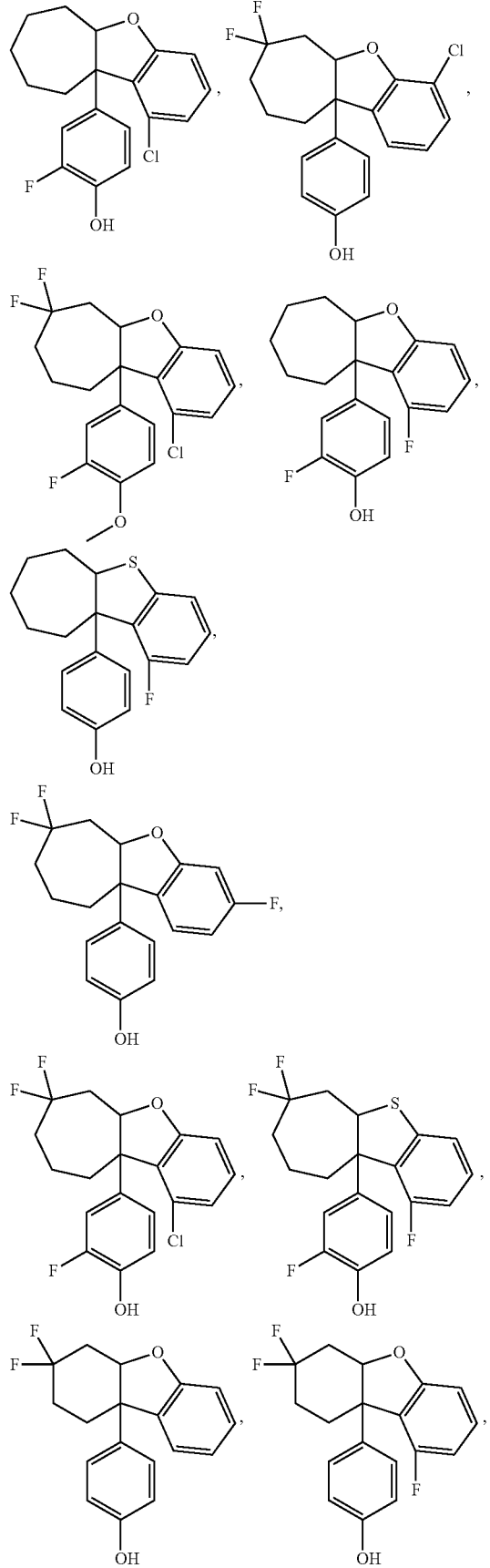

-continued
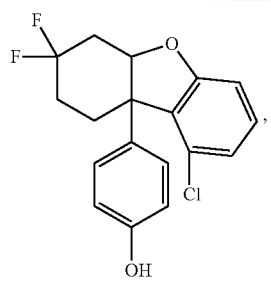
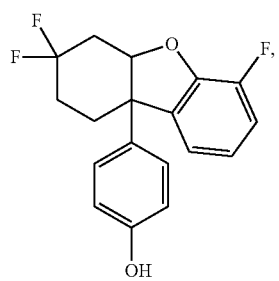
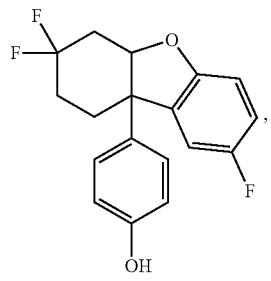
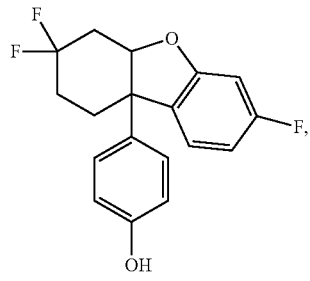
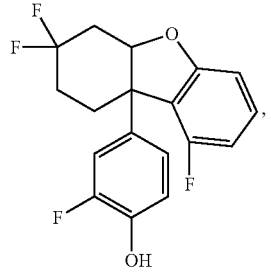 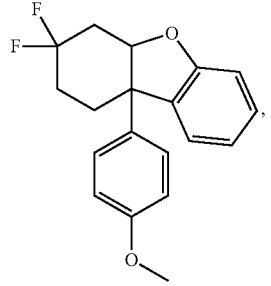
-continued
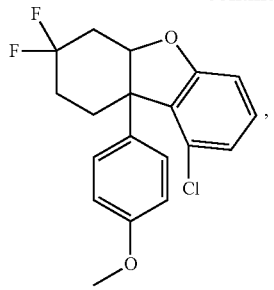
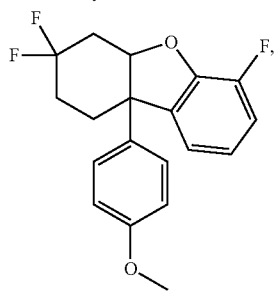
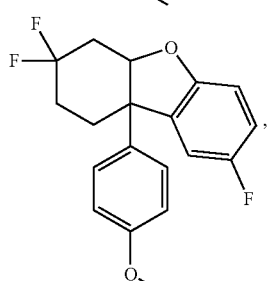
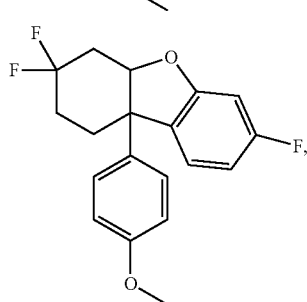
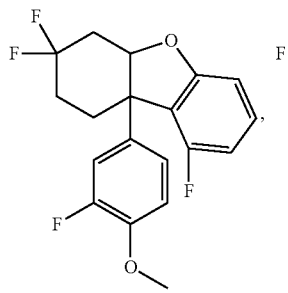 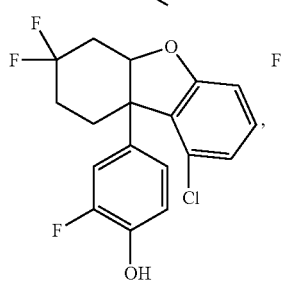

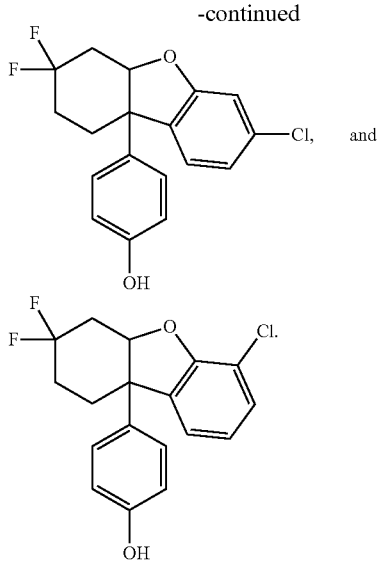

In some embodiments, the subject to be treated is a human.

In some embodiments, the ERβ agonist is administered topically, whereas in other embodiments, the ERβ agonist is administered intraperitoneally. In other embodiments, the ERβ agonist is administered orally.

The term "subject" refers to an animal, preferably a mammal, and most preferably a human, who is the object of treatment, observation or experiment. The mammal may be selected from the group consisting of mice, rats, rabbits, guinea pigs, dogs, cats, sheep, goats, cows, primates, such as monkeys, chimpanzees, and apes, and humans.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated.

Another embodiment is a method of identifying a compound that regulates activity of an Estrogen receptor by culturing cells that express the Estrogen receptors; incubating the cells with at least one compound of Formula I as defined herein; and determining any change in activity of the Estrogen receptors so as to identify a compound of Formula I which regulates activity of a Estrogen receptors.

EXAMPLES

Embodiments of the present invention are disclosed in further detail in the following examples, which are not in any way intended to limit the scope of the invention.

As employed herein, the following terms have their accepted meaning in the chemical literature.

| | |
|---|---|
| AcOH | Acetic acid |
| anhyd | anhydrous |
| CDI | 1,1'-carbonyldiimidazole |
| DCM | Dichloromethane |
| DMF | N,N-Dimethylformamide |
| DMAP | 4-Dimethylaminopyridine |
| DMPU | 1,3-Dimethyl-3,4,5,6-tetrahydro-1(1H)-pyrimidinone |
| DMSO | Dimethyl sulfoxide |
| EDCl | 1-(3-Dimethylaminopropyl)-3-ethylcarbodiimide hydrochloride |
| Et$_2$O | Diethyl ether |
| EtOAc | Ethyl acetate |
| EtOH | Ethanol |
| KHMDS | Potassium hexamethyldisilazide |
| mCPA | 3-Chloroperbenzoic acid |
| MeOH | Methanol |
| MeCN | Acetonitrile |
| NH$_4$OAc | Ammonium acetate |
| NMM | N-Methylmorpholine |
| HOBt | 1-Hydroxybenztriazole |
| Pd/C | Palladium on activated carbon |
| TEA | Triethylamine |
| TFA | Trifluoroacetic acid |
| THF | Tetrahydrofuran |
| uW, MW | Microwave reactor chemistry |

Example 1

Analytical Procedure

Analyses were performed on a combined prep/analytical Waters/Micromass system consisting of a ZMD single quadropole mass spectrometer equipped with electro-spray ionization interface. The HPLC system consisted of a Waters 600 gradient pump with on-line degassing, a 2700 sample manager and a 996 PDA detector.

Separation was performed on an X-Terra MS C18, 5 μm 4.6×50 mm column. Buffer A: 10 mM ammonium acetate in water, buffer B: 10 mM ammonium acetate in acetonitrile/water 95/5. A gradient was run from 10% B to 100% B in 10 min, stay at 100% B for 1 min, re-equilibrate for 6 min. The system was operated at 1 mL/min.

For some analyses, separation was performed on an X-Terra MS C18, 5 μm 4.6×50 mm column. Buffer A: 10 mM ammonium acetate in water, buffer B: 10 mM ammonium acetate in acetonitrile/water 95/5. A gradient was run from 30% B to 100% B in 7 min, stay at 100% B for 1 min, re-equilibrate for 5.5 min. The system was operated at 1 mL/min.

Example 2

(4-Benzyloxy-phenyl)-phenyl-methanone (1)

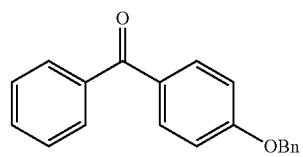

1

The standard procedure for the benzylation of phenols is exemplified by the synthesis of (4-Benzyloxy-phenyl)-phenyl-methanone (1).

NaH (60% in mineral oil, 1.2 g, 30 mmol) was added to an ice-cooled solution of (4-hydroxy-phenyl)-phenyl-methanone (5 g, 25.2 mmol) in DMF (25 mL). The resulting mixture was stirred for 20 minutes at room temperature (r.t.). Benzyl bromide (6.1 mL, 50 mmol) was added at 0° C. The reaction temperature was raised to r.t. after 1 h and thereafter stirred for additional 2 h. Water (20 mL) was added and the aqueous phase was extracted with dichloromethane (2×30 mL). The combined organic phase was concentrated and purified by flash chromatography (eluent: 100% dichloromethane). Yield: 7.0 g, 96% of 1. ¹H NMR (400 MHz, CDCl₃): δ 7.83 (d, J=8.4 Hz, 2H), 7.77 (d, J=7.2 Hz, 2H), 7.58-7.52 (m, 1H), 7.50-7.32 (m, 7H), 7.03 (d, J=8.4 Hz, 2H), 5.17 (s, 2H).

Example 3

(4-Benzyloxy-phenyl)-2-fluorophenyl-methanone (2)

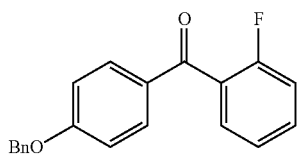

The title compound 2 was synthesized from (2-fluorophenyl)(4-hydroxyphenyl)methanone (2.0 g) using the procedure described for the synthesis of compound 1. Yield: 2.4 g, (96%). ¹H-NMR (400 MHz, CDCl₃): δ ppm 7.86-7.72 (m, 2H), 7.50-7.42 (m, 2H), 7.41-7.28 (m, 5H), 7.25-7.17 (m, 1H), 7.15-7.07 (m, 1H), 7.02-6.94 (m, 2H), 5.10 (s, 2H).

Example 4

(4-(Benzyloxy)phenyl)(2,3-difluorophenyl)methanone (3)

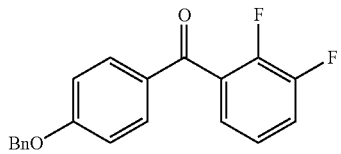

A solution of t-butyllithium (3.0 mL, 1.2 M in pentane) was added to a cooled (−78° C.) solution of benzyloxy-4-bromobenzene (500 mg, 1.9 mmol) in THF (20 mL). The temperature was raised to −15° C. over a period of 1 h and stirred at −15° C. for an additional 2 h. A slurry of MnCl₂.2LiCl₂ (1.9 mmol) in THF (13 mL) was added and the mixture was stirred for 30 min allowing the temperature to reach 0° C. 2,3-Difluorobenzoyl chloride was added and the reaction was stirred at r.t. for 1 h. Water (20 mL) was added, stirred for 10 min. The aqueous phase was extracted with dichloromethane (2×20 mL) and the organic phases were combined and washed with brine (20 mL), dried (Na₂SO₄), filtered and concentrated. Purified by flash chromatography (eluent: 100% heptane→10% ethyl acetate in heptane) to give the title compound 3 (320 mg, 52% yield). ¹H-NMR (400 MHz, CDCl₃): δ 7.88 (d, J=7.5 Hz, 2H), 7.48-7.15 (m, 8H), 7.08 (d, J=7.5 Hz, 2H), 5.18 (s, 2H).

Example 5

(4-(Benzyloxy)phenyl)(2,5-difluorophenyl)methanone (4)

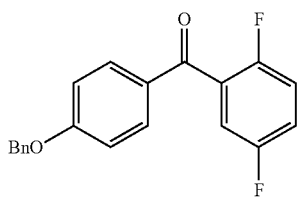

The title compound was prepared according to the procedure as described for the synthesis of 3. Yield: 510 mg, (83%). ¹H-NMR (400 MHz, CDCl₃): δ d 7.88 (d, J=7.5 Hz, 2H), 7.49-7.34 (m, 5H), 7.28-7.10 (m, 3H), 7.05 (d, J=7.5 Hz, 2H), 5.18 (s, 2H).

Example 6

(2,6-Difluorophenyl)(4-(tetrahydro-2H-pyran-2-yloxy)phenyl)-methanone (5)

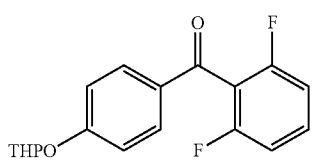

A solution of ZnBr₂ in THF (1.5 M, 2 mL, 3.0 mmol) was added to a solution of (4-(tetrahydro-2H-pyran-2-yloxy)phenyl)magnesium bromide in THF (0.2 M, 15 mL, 3 mmol) under an atomsphere of argon at r.t. The reaction mixture was stirred for 10 minutes, cooled with a dry-ice acetone bath. Palladium tetrakistriphenylphosphine (50 mg) and a solution of 2,6-difluorobenzoyl chloride (0.37 mL, 3 mmol) in THF (2 mL) were added. The mixture was stirred over night at r.t. The organic phase was washed with brine (2×20 mL), dried (Na₂SO₄) and concentrated yielding a solid. Purified by flash chromatography (eluent: heptane→20% ethyl acetate in heptane). Yield: 318 mg, 33% (approx. 85% pure according to ¹H-NMR). ¹H-NMR (400 MHz, CDCl₃): δ 7.83-7.78 (m, 2H), 7.49-7.38 (m, 1H), 7.14-7.07 (m, 2H), 7.03-6.95 (m, 2H), 5.52 (t, J=3.1 Hz, 1H), 3.83-3.80 (m, 1H), 3.63-3.58 (m, 1H), 2.10-1.90 (m, 1H), 1.89-1.85 (m, 2H), 1.72-1.58 (m, 3H).

Example 7

1-((4-(Benzyloxy)phenyl)(cyclohexylidene)methyl)-2-fluorobenzene (6)

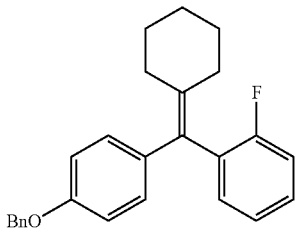

Procedure A

A three-necked, round-bottom flask (100 mL) containing zinc powder (1.2 g, 18 mmol) was fitted with a reflux condenser, was evacuated for 10 min. and charged with argon. THF (15 mL) was added, the reaction mixture was cooled (−10° C.) and titanium(IV) chloride (1.64 g, 8.62 mmol) was added dropwise (yellow fume released). The mixture turned yellow-green. The reaction mixture was heated at 100° C. for 1 h and then cooled to r.t. A solution of 4-benzyloxy-2'-fluorobenzophenone (600 mg, 2.0 mmol) and cyclohexanone (500 mg, 3.4 mmol) in THF (15 mL) was added, the mixture was heated for 50 min at 100° C. and then cooled to r.t. TLC indicated full conversion of the benzophenone. The cooled mixture was poured into a saturated aqueous solution of NaHCO$_3$ (200 mL). Ethyl acetate (20 mL) was added. The organic phase was decanted off and washed with water (2×50 mL), dried (Na$_2$SO$_4$) and concentrated to a light yellow syrup. Work-up by flash chromatography (eluent: 5% ethyl acetate in heptane) afforded the title compound in yield of 0.75 g, quantitatively. $^1$H-NMR (400 MHz, CDCl$_3$): δ 7.49-7.20 (m, 5H), 7.10-6.99 (m, 4H), 6.98-6.86 (m, 2H), 6.83-6.77 (m, 2H), 4.96 (s, 2H), 2.20 (broad s, 2H), 2.01 (broad s, 2H), 1.52 (broad s, 6H).

Procedure B

CeCl$_3$ (310 mg, 0.83 mmol) was added to a cooled solution (0° C.) of cyclohexyl magnesium bromide (1 mmol) and THF (10 mL) and the resulting mixture was stirred for 10 min at 0° C. A solution of 4-O-benzyl-2'-fluoro benzophenone (250 mg, 0.81 mmol) in THF (10 mL) was added to the ice cooled mixture. The mixture was stirred for 20 min. A solution of aqueous HCl (1M, 10 mL) was added and the mixture was stirred for ½ h, then extracted with dichloromethane (2×20 mL). The combined organic phase was dried (Na$_2$SO$_4$) and concentrated in vacuo to a syrup. $^1$H-NMR showed a mixture of compounds. The mixture was dissolved in dichloromethane (20 mL) and TFA (2 mL), stirred for 1 h at room tempature, concentrated to a syrup. Purification by combiflash chromatography (eluent: 5→15% ethyl acetate in heptane) afforded the title product in a yield of: 240 mg (77%).

Example 8

4-(Cyclohexylidene(2,6-difluorophenyl)methyl)phenol (7)

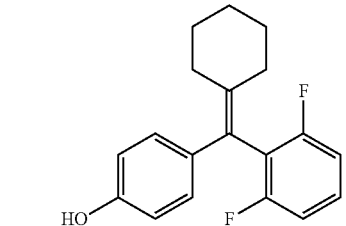

The title compound 7 was synthesized from benzophenone 5 (289 mg) using procedure B described for the synthesis of compound 6. The THP protection group was cleaved under the acidic conditions used in the work-up. Yield: 78 mg (29%) $^1$H-NMR (400 MHz, CDCl$_3$): δ ppm 7.30-7.14 (m, 3H), 6.88-6.81 (m, 2H), 6.77-6.71 (m, 2H), 4.85 (s, 1H), 2.27 (d, J=5.38 Hz, 2H), 2.05 (d, J=5.85 Hz, 2H), 1.71-1.52 (m, 6H).

Example 9

2-((4-(Benzyloxy)phenyl)(cyclohexylidene)methyl)-1,4-difluoro-benzene (8)

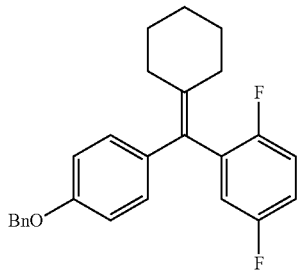

The title compound 8 was synthesized from ketone 4 (500 mg) using procedure A described for the synthesis of compound 6. Yield: 410 mg (68%). $^1$H-NMR (400 MHz, CDCl$_3$): δ ppm 7.37-7.18 (m, 5H), 7.02-6.95 (m, 2H), 6.93-6.83 (m, 2H), 6.83-6.72 (m, 3H), 4.92 (s, 2H), 2.18 (broad s, 2H), 2.03-1.95 (m, 2H), 1.55-1.38 (m, 6H).

Example 10

1-((4-(Benzyloxy)phenyl)(cyclohexylidene)methyl)-2,3-difluoro-benzene (9)

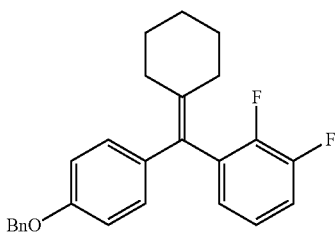

Compound 9 was synthesized from ketone 3 (320 mg) using procedure A described for the synthesis of 6. Yield: 210 mg (55%). ¹H-NMR (400 MHz, CDCl₃): δ ppm 7.34-7.17 (m, 5H), 7.01-6.94 (m, 2H), 6.90-6.77 (m, 3H), 6.77-6.67 (m, 2H), 4.91 (s, 2H), 2.21-2.11 (m, 2H), 2.01-1.97 (m, 2H), 1.56-1.39 (m, 6H)

Example 11

4-(Cyclopentylidene(2,6-difluorophenyl)methyl)phenol (12)

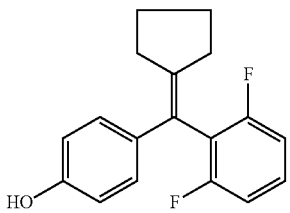

Compound 12 was synthesized from ketone 5 (1 mmol) and cyclopentyl magnesium bromide (2 mmol) using procedure B described for synthesis of 6. The THP protection group was cleaved under the acidic conditions used. Yield: 18 mg (16%). ¹H-NMR (400 MHz, CDCl₃): δ ppm 7.26-7.14 (m, 1H), 7.13-7.12 (m, 2H), 6.89-6.85 (m, 2H), 6.76-6.73 (m, 2H), 4.75 (s, 1H), 2.50 (broad t, J=6.4 Hz, 2H), 2.13 (broad t, J=6.4 Hz, 2H), 1.75-1.58 (m, 4H).

Example 12

1-((4-(Benzyloxy)phenyl)(cyclopentylidene)methyl-2-fluorobenzene (13)

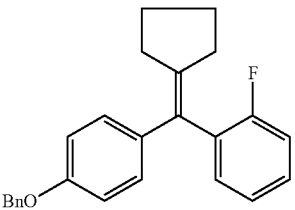

Compound 13 was synthesized from ketone 2 (1 g, 3.3 mmol) and cyclopentyl magnesium bromide (6.6 mmol) using procedure B described for synthesis of 6. Yield: 180 mg (17%). ¹H-NMR (400 MHz, CDCl₃): δ ppm 7.49-7.29 (m, 5H), 7.25-7.13 (m, 3H), 7.11-7.02 (m, 2H), 6.94-6.87 (m, 3H), 5.04 (s, 2H), 2.53-2.47 (m, 2H), 2.22-2.17 (m, 2H), 1.80-1.58 (m, 4H)

Example 13

2-(4-(Benzyloxy)phenyl)-2-(2-fluorophenyl)cycloheptanone (14)

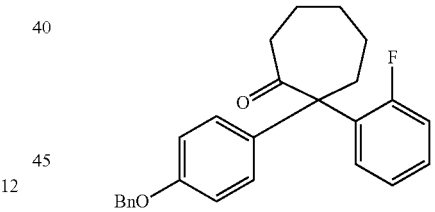

Procedure C

Compound 6 (240 mg, 0.64 mmol) was dissolved in dichloromethane (50 mL) and m-chloroperbenzoic acid (220 mg, 128 mmol, 2 eqiuv) was added. The mixture was stirred at r.t. for 3 h (TLC indicated full conversion of the starting material). TFA (0.5 mL) was added. The mixture was stirred for 10 min. Saturated NaHCO₃ (20 mL) and 10% aqueous Na₂S₂O₇ (10 mL) were added and the mixture was stirred for 10 min. The aqueous phase was separated off and the organic phase was dried (Na₂SO₄) and concentrated to a syrup. Purification by combiflash chromatography (eluent: 5→15% ethyl acetate in heptane) afforded the title product in a yield of: 248 mg, quantitatively. ¹H-NMR (400 MHz, CDCl₃): δ ppm 7.39-7.22 (m, 5H), 7.19-7.05 (m, 1H), 7.05-7.02 (m, 2H), 6.98-6.85 (m, 3H), 6.84-6.80 (m, 2H), 4.96 (s, 2H), 2.74-2.40 (m, 4H), 1.78-1.58 (m, 6H).

Example 14

2-(2,6-Difluorophenyl)-2-(4-hydroxyphenyl)cycloheptanone (15)

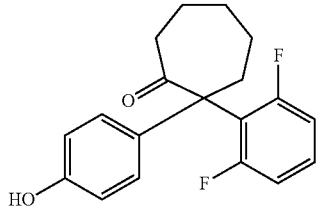

15

The title compound 15 was synthesized from compound 7 (78 mg) using procedure C described for the synthesis of compound 14. Yield: 45 mg (60%). $^1$H-NMR (400 MHz, CDCl$_3$): δ ppm 7.21 (tt, J=8.46, 8.46, 6.07, 6.07 Hz, 1H), 6.91-6.78 (m, 2H), 7.06-6.98 (m, 2H), 6.73-6.62 (m, 2H), 3.15 (tdd, J=14.83, 10.18, 2.24, 2.24 Hz, 1H), 2.79-2.65 (m, 2H), 2.29 (dd, J=15.19, 9.22 Hz, 1H), 1.93-1.44 (m, 6H).

Example 15

2-(4-(Benzyloxy)phenyl)-2-(2,5-difluorophenyl)cycloheptanone (16)

16

The title compound 16 was synthesized from 8 (410 mg) using procedure C described for the synthesis of 14. Yield: 230 mg (54%). $^1$H-NMR (400 MHz, CDCl$_3$): δ ppm 7.48-7.29 (m, 5H), 7.21-7.14 (m, 2H), 7.14-7.03 (m, 1H), 7.01-6.83 (m, 3H), 6.70-6.60 (m, 1H), 5.05 (s, 2H), 2.77 (ddd, J=12.30, 9.59, 2.75 Hz, 1H), 2.69-2.56 (m, 1H), 2.56-2.48 (m, 1H), 2.47-2.40 (m, 1H), 1.99-1.36 (m, 6H).

Example 16

2-(4-(Benzyloxy)phenyl)-2-(2,3-difluorophenyl)cycloheptanone (17)

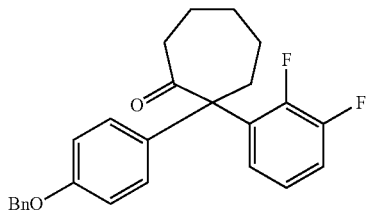

17

The title compound 17 was synthesized from 9 (210 mg) using procedure C described for the synthesis of compound 14. Yield: 110 mg (50%). $^1$H-NMR (400 MHz, CDCl$_3$): δ ppm 7.49-7.29 (m, 5H), 7.22-7.14 (m, 2H), 7.13-7.01 (m, 1H), 6.99-6.91 (m, 3H), 6.71 (tdd, J=8.06, 6.42, 1.66, 1.66 Hz, 1H), 5.05 (s, 2H), 2.78 (ddd, J=12.34, 9.85, 2.57 Hz, 1H), 2.73-2.59 (m, 2H), 2.53 (dd, J=15.19, 8.89 Hz, 1H), 1.90-1.17 (m, 6H).

Example 17

2-(2,6-Difluorophenyl)-2-(-4-hydroxyphenyl)cyclohexanone (18)

18

The title compound 18 was synthesized from phenol 12 (18 mg) using procedure C described for the synthesis of 14. Yield: 14 mg (74%). $^1$H-NMR (400 MHz, CDCl$_3$): δ ppm 7.29-7.20 (m, 1H), 7.18-7.10 (m, 2H), 6.86 (dd, J J=8 Hz, J=9 Hz, 2H), 6.78-6.72 (m, 2H), 4.93 (broad s, 1H), 3.08-2.98 (m, 1H), 2.68-2.61 (m, 1H), 2.51-2.43 (m, 1H), 2.42-2.34 (m, 1H), 2.05-1.57 (m, 4H).

Example 18

2-(4-(Benzyloxy)phenyl)-2-(2-fluorophenyl)cyclohexanone (19)

19

The title compound 19 was synthesized from 13 (180 mg) using procedure C described for the synthesis of 14. Yield: 165 mg (79%). ¹H-NMR (400 MHz, CDCl₃): δ ppm 7.52-7.30 (m, 5H), 7.30-7.15 (m, 3H), 7.07-7.01 (m, 3H), 6.94-6.89 (m, 1H), 6.38 (dt, J=7.85, 7.85, 1.73 Hz, 1H), 5.09 (s, 2H), 2.71-2.47 (m, 3H), 2.40 (ddd, J=14.76, 10.58, 7.22 Hz, 1H), 2.00-1.91 (m, 2H), 1.86-1.79 (m, 2H).

Example 19

2-(2-Fluorophenyl)-2-(4-hydroxyphenyl)cycloheptanone (20)

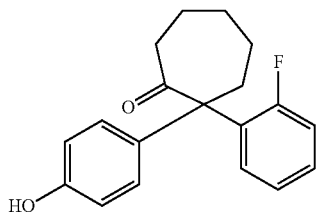

Compound 14 (10 mg) was dissolved in methanol (10 mL) and ethyl acetate (5 mL). 5% Palladium on carbon (10 mg) was added. Nitrogen was bubbled through the solution. A balloon filled with hydrogen was fitted to the system. The mixture was stirred over night, then filtered through a plug of celite and concentrated to a solid. ¹H-NMR indicated full conversion to the title compound 20. ¹H-NMR (400 MHz, CDCl₃): δ ppm 7.25-7.18 (m, 1H), 7.15-7.08 (m, 2H), 7.05-6.95 (m, 3H), 6.78-6.72 (m, 2H), 2.74-2.43 (m, 4H), 1.80-1.58 (m, 6H).

Example 20

2-(2-Fluorophenyl)-2-(4-hydroxyphenyl)cyclohexanone (21)

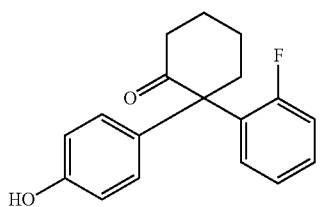

The title compound 21 was synthesized from compound 19 (5 mg) using the procedure described for the synthesis of compound 20. Yield: 3 mg. ¹H-NMR (400 MHz, CDCl₃): δ ppm 7.16-7.06 (m, 3H), 6.97 (ddd, J=11.76, 8.14, 1.28 Hz, 1H), 6.90-6.73 (m, 3H), 6.31 (dt, J=7.87, 7.86, 1.74 Hz, 1H), 4.92 (s, 1H), 2.69-2.40 (m, 2H), 2.41-2.23 (m, 2H), 1.95-1.82 (m, 2H), 1.83-1.69 (m, 2H).

Example 21

(E)-10a-(4-(Benzyloxy)phenyl)-1-fluoro-8,9,10,10a-tetrahydro-7H-benzo[b]-cyclohepta[d]furan (22)

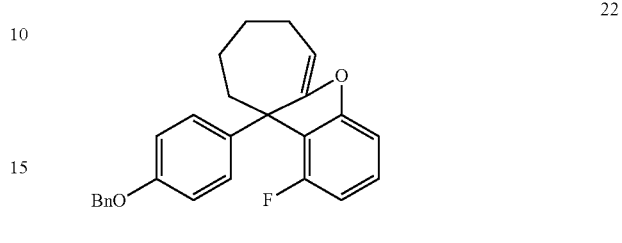

KHMDS (0.2 mL, 0.5 M in toluene) was added to a solution of 2-(4-(benzyloxy)phenyl)-2-(2,6-difluorophenyl)cycloheptanone (50 mg) in toluene (3 mL) and DMPU (1 mL). The reaction mixture was heated at 90° C. for 2 h (TLC indicated some conversion of the starting material). Additional heating for 1 h gave no further conversion of the starting material according to TLC. The organic phase was washed with water (10 mL), brine, dried (Na₂SO₄) and concentrated in vacuo. Work-up by flash chromatography (eluent heptane dichloromethane 1:1) afforded the title compound 22 in a yield of 20 mg. ¹H-NMR (400 MHz, CDCl₃): δ ppm 7.49-7.46 (m, 2H), 7.50-7.34 (m, 5H), 7.10-7.00 (m, 1H), 6.96-6.91 (m, 2H), 6.61-6.59 (m, 1H), 6.53-6.48 (m, 1H), 5.73 (dd, J=5, 9 Hz, 1H), 5.02 (s, 2H), 3.07-3.02 (m, 1H), 2.00-1.20 (m, 8H).

Example 22

(E)-4-(1-Fluoro-8,9,10,10a-tetrahydro-7H-benzo[b] cyclohepta-[d]furan-10a-yl)phenol (349)

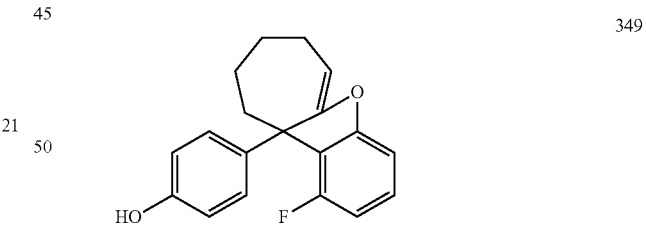

10% Palladium on activated carbon (few mg) was added to a solution of 22 (15 mg) in ethyl acetate (2 mL) and ethanol (2 mL). A balloon filled with H₂ was fitted and H₂ was bubbled through the solution for 15 s. The mixture was filtered after 15 min, TLC indicated 50% conversion of 22. Work-up by flash chromatography (eluent: dichloromethane ->5% ethyl acetate in dichloromethane) afforded 8 mg of the title product. Starting material (5 mg) was recovered. LC-MS confirmed m/z=295 (M-1). ¹H-NMR (400 MHz, CDCl₃): δ ppm 7.49-7.46 (m, 2H), 7.05-7.00 (m, 1H), 6.81-6.79 (m, 2H), 6.61-6.59 (m, 1H), 6.53-6.48 (m, 1H), 5.73 (dd, J=4.8, 9.2 Hz, 1H), 3.07-3.02 (m, 1H), 2.00-1.20 (m, 8H).

Example 23

2-(4-(Benzyloxy)phenyl)-2-(2-fluorophenyl)cycloheptanol (23) and 2-(2-fluorophenyl)-2-(4-hydroxyphenyl)cycloheptanol (24)

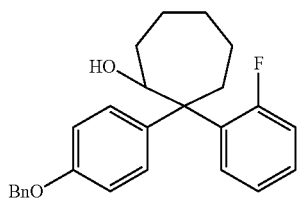

23

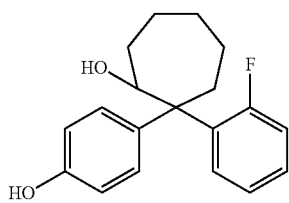

24

Procedure D

A solution of LiALH₄ (1M, 0.15 mL) was added to compound 14 (60 mg, 0.15 mmol) in THF (5 mL). The mixture was stirred for 2 h. The reaction was quenched with water (4 mL) and the reaction mixture was extracted with diethyl acetate (20 mL). The organic phase was dried (Na$_2$SO$_4$) and concentrated to a solid. The alcohol 23 was obtained after flash chromatography (eluent: heptane: ethyl acetate 1:0→4:1). Yield: 25 mg. The debenzylated compound 24 was also isolated in a yield of 10 mg. 23: $^1$H-NMR (400 MHz, CDCl$_3$): δ ppm 8.03-7.98 (m, 1H), 7.48-7.22 (m, 6H), 7.18-7.12 (m, 1H), 7.06-7.02 (m, 2H), 6.99-6.93 (m, 1H), 6.90-6.86 (m, 2H), 5.02 (s, 2H), 4.12 (dd, J=3.4, 10.3 Hz, 1H), 2.54-2.14 (m, 4H), 1.84-1.48 (m, 6H). 24: $^1$H-NMR (400 MHz, CDCl$_3$): δ 8.02-7.95 (m, 1H), 7.29-7.22 (m, 1H), 7.18-7.11 (m, 1H), 7.01-6.92 (m, 3H), 6.76-6.70 (m, 2H), 5.68 (s, 2H), 4.10 (dd, J=4, 10 Hz, 1H), 2.54-2.14 (m, 4H), 1.82-1.48 (m, 6H).

Example 24

2-(2,6-Difluorophenyl)-2-(4-hydroxyphenyl)cycloheptanol (25)

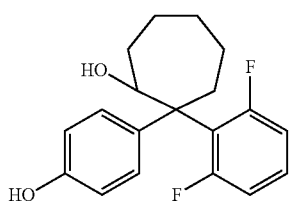

25

The title compound 25 was synthesized from ketone 15 (45 mg) using procedure D described for the synthesis of 23/24. Yield: 20 mg (44%). The product was a mixture of two enantiomeric pairs which were seperated by flash chromatography (eluent: 5% ethyl acetate in dichloromethane, R$_F$ 0.20 and 0.22). The enantiomeric mixture 25A (R$_F$=0.22). Yield: 10 mg. $^1$H-NMR (400 MHz, CDCl$_3$): δ ppm 7.29-7.12 (m, 1H), 7.08-6.97 (m, 2H), 6.89-6.78 (m, 2H), 6.72-6.64 (m, 2H), 4.74 (s, 1H), 4.41 (t, J=6.95 Hz, 1H), 2.65-2.55 (m, 1H), 2.35-2.26 (m, 1H), 2.23-2.03 (m, 2H), 1.88-1.80 (m, 2H), 1.62-1.50 (m, 4H). The enantiomeric mixture 25B (R$_F$=0.20). Yield: 4 mg. $^1$H-NMR (400 MHz, CDCl$_3$): δ ppm 7.24-7.11 (m, 3H), 6.81 (dd, J=11.17, 8.26 Hz, 1H), 6.78-6.69 (m, 2H), 4.85-4.70 (m, 1H), 2.73-2.59 (m, 1H), 2.58-2.43 (m, 1H), 2.15-2.01 (m, 1H), 2.01-1.90 (m, 1H), 1.90-1.67 (m, 2H), 1.68-1.41 (m, 4H)

Example 25

2-(4-(Benzyloxy)phenyl)-2-(2,5-difluorophenyl)cycloheptanol (26)

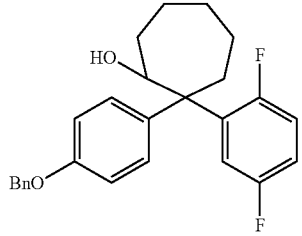

26

The title compound 26 was synthesized from ketone 16 (230 mg) using procedure D described for the synthesis of 23/24. Yield: 180 mg (77%). $^1$H-NMR (400 MHz, CDCl$_3$): δ ppm 7.85-7.73 (m, 1H), 7.47-7.28 (m, 5H), 7.08-6.99 (m, 2H), 6.99-6.82 (m, 4H), 5.02 (s, 2H), 4.10-4.02 (m, 1H), 2.54-2.40 (m, 1H), 2.40-2.27 (m, 1H), 2.25-2.08 (m, 2H), 1.90-1.17 (m, 6H)

Example 26

2-(4-(Benzyloxy)phenyl)-2-(2,3-difluorophenyl)cycloheptanol (27)

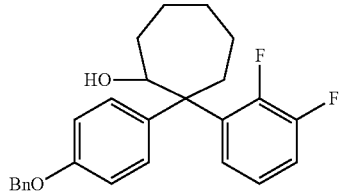

27

The title compound 27 was synthesized from ketone 17 (110 mg) using procedure D described for the synthesis of 23/24. The product consisted of two pairs of enantiomers (ratio of 4:1 according to $^1$H-NMR). Major isomer: $^1$H-NMR (400 MHz, CDCl$_3$): δ ppm 7.83-7.73 (m, 1H), 7.50-7.29 (m, 5H), 7.11-7.00 (m, 4H), 6.94-6.86 (m, 2H), 5.03 (s, 2H), 4.08 (dd, J=8.68, 4.41 Hz, 1H), 2.55-2.44 (m, 1H), 2.41-2.31 (m, 1H), 2.24-2.13 (m, 2H), 1.78-1.09 (m, 6H)

Example 27

4-(1-(2,6-Difluorophenyl)-2-hydroxycyclohexyl)phenol

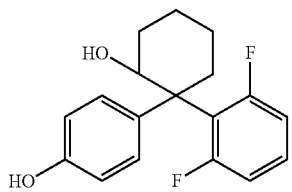

28

The title compound 28 was synthesized from ketone 18 (12 mg) using procedure D described for the synthesis of 23/24. Yield: 10 mg (82%). $^1$H-NMR (400 MHz, CDCl$_3$): δ ppm 7.30-7.21 (m, 2H), 7.18-7.08 (m, 1H), 6.82-6.72 (m, 4H), 4.96 (broad s, 1H), 4.78 (s, 1H), 2.72-2.64 (m, 2H), 2.04-1.30 (m, 6H).

Example 28

2-(4-(Benzyloxy)phenyl)-2-(2-fluorophenyl)cyclohexanol (29) and 4-(1-(2-Fluorophenyl)-2-hydroxycyclohexyl)phenol (30)

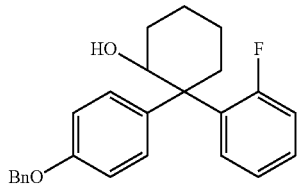

29

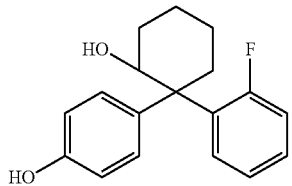

30

The benzyl protected title compound 29 was synthesized from ketone 19 (155 mg) using procedure D described for the synthesis of 23/24. Yield: 130 mg (80%). 7 mg of the debenzylated compound 30 was isolated and the two enantiomeric pairs of 30 were separated by flash chromatography. The enantiomeric mixture A with the highest R$_F$ value (4 mg), LC-MS m/z=285 (M−1). $^1$H-NMR (400 MHz, CDCl$_3$): δ ppm 7.84 (dt, J=8.04, 7.98, 1.91 Hz, 1H), 7.23-7.17 (m, 1H), 7.17-7.10 (m, 3H), 6.90 (ddd, J=12.91, 7.97, 1.56 Hz, 1H), 6.76-6.71 (m, 2H), 4.71 (s, 1H), 4.64-4.53 (m, 1H), 2.62-2.54 (m, 1H), 2.26-2.19 (m, 1H), 2.09-2.03 (m, 1H), 1.82-1.68 (m, 1H), 1.51-1.33 (m, 4H). The enantiomeric mixture B with the lowest R$_F$ value (3 mg), LC-MS/UV m/z=285 (M−1). $^1$H-NMR (400 MHz, CDCl$_3$): δ ppm 7.39 (dt, J=8.21, 8.07, 1.71 Hz, 1H), 7.29-7.22 (m, 2H), 7.21-7.14 (m, 1H), 7.12-7.06 (m, 1H), 6.91 (ddd, J=13.08, 8.01, 1.49 Hz, 1H), 6.78-6.73 (m, 2H), 4.75-4.69 (m, 1H), 2.61-2.36 (m, 2H), 2.08-1.97 (m, 1H), 1.96-1.87 (m, 1H), 1.82-1.11 (m, 4H).

Example 29

10a-(4-(benzyloxy)phenyl)-6,7,8,9,10,10a-hexahydro-5aH-benzo-[b]cyclohepta[d]furan (31)

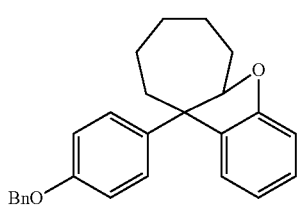

31

Procedure E

DMPU (100 μl) and tBuOK (60 mg) were added to a solution of alcohol 23 (60 mg, 0.15 mmol) in toluene (5 mL). The mixture was stirred at 80° C. for ½ h. (TLC indicated full conversion of starting material), concentrated in vacuo and purified by flash chromatography (eluent: 10% dichloromethane in heptane) hereby affording the title compound in a yield of: 45 mg, 77%. $^1$H-NMR (400 MHz, CDCl$_3$): δ 7.46-7.31 (m, 5H), 7.25-7.17 (m, 3H), 7.01-6.98 (m, 1H), 6.94-6.86 (m, 4H), 5.04 (s, 2H), 4.94 (dd, J=3, 11 Hz, 1H), 2.45-2.37 (m, 1H), 2.26-2.10 (m, 2H), 1.94-1.85 (m, 1H), 1.80-1.28 (m, 6H).

Example 30

4-(1-Fluoro-6,7,8,9,10,10a-hexahydro-5aH-benzo[b]cyclohepta[d]-furan-10a-yl)phenol (231 (982 and 983) and 232)

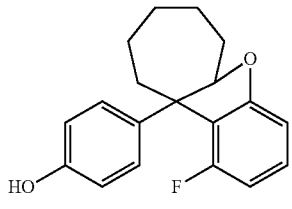

231 (982 and 983) and 232

Compound mixtures 231 (982 and 983) and 232 were synthesized from the isolated enantiomeric mixtures 25A and 25B (10 mg and 4 mg), respectively, using procedure E described for the synthesis of compound 31. Yield: 231 (2.3 mg) and 232 (0.8 mg).

The enantiomeric mixture 231. Yield: 2.3 mg. LC MS/UV, m/z=299 (M+1). $^1$H-NMR (400 MHz, CDCl$_3$): δ ppm 7.20-7.08 (m, 3H), 6.80-6.71 (m, 2H), 6.64 (dd, J=8.06, 0.80 Hz, 1H), 6.55 (ddd, J=9.34, 8.28, 0.79 Hz, 1H), 4.90 (dd, J=6.60, 1.77 Hz, 1H), 4.71 (s, 1H), 2.39-2.31 (m, 2H), 2.16 (s, 1H), 1.91-1.80 (m, 1H), 1.76-1.25 (m, 6H).

The enantiomers of 231 were separated by Chiral-HPLC to give 982 (1.0 mg) and 983 (1.0 mg), conditions see below. Analytical retention times; 982 (13.2 minutes) and 983 (16.2 minutes).

| Analytical | |
|---|---|
| Column | ChiralPak AD (4.6 × 250 mm) |
| Mobile phase | Heptane-IPA (95:5) |
| Flow | 1 mL/min. |
| Detection | 230 nm |

| Preparative | |
|---|---|
| Column | ChiralPak AD (10 × 250 mm) |
| Mobile phase | Heptane-IPA (95:5) |
| Flow | 5 mL/min. |
| Detection | 230 nm |
| Inj. vol. | 100 mg/mL |
| Conc. | 1.5 mg/mL |
| Loading | 0.15 mg |

The enantiomeric mixture 232. Yield: 0.8 mg. LC MS/UV: m/z=299 (M+1) was confirmed. $^1$H-NMR (400 MHz, CDCl$_3$): δ ppm 6.81-6.74 (m, 2H), 6.51 (dt, J=6.62, 6.57, 4.62 Hz, 1H), 6.29-6.26 (m, 2H), 6.20 (dd, J=6.43, 0.57 Hz, 1H), 6.07-5.99 (m, 1H), 4.88-4.81 (m, 1H), 4.61 (s, 1H), 3.58-3.46 (m, 1H), 2.72-2.57 (m, 2H), 2.49-1.68 (m, 7H).

Example 31

10a-(4-(benzyloxy)phenyl)-2-fluoro-6,7,8,9,10,10a-hexahydro-5aH-benzo[b]cyclohepta[d]furan (32)

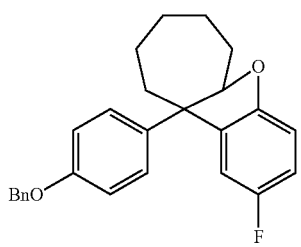

32

The title compound 32 was synthesized from 26 (180 mg) using procedure E described for the synthesis of compound 31. Yield: 141 mg (82%). $^1$H-NMR (400 MHz, CDCl$_3$): δ ppm 7.45-7.28 (m, 5H), 7.23-7.17 (m, 2H), 6.93-6.89 (m, 2H), 6.85 (dt, J=8.84, 8.78, 2.74 Hz, 1H), 6.75 (dd, J=8.70, 4.21 Hz, 1H), 6.66 (dd, J=8.20, 2.75 Hz, 1H), 5.04 (s, 2H), 4.95 (dd, J=7.29, 1.60 Hz, 1H), 2.37 (dd, J=14.43, 10.44 Hz, 1H), 2.17 (td, J=14.82, 7.50, 7.50 Hz, 1H), 2.08 (dd, J=14.61, 8.46 Hz, 1H), 1.85 (tdd, J=14.54, 11.13, 1.54, 1.54 Hz, 1H), 1.79-1.08 (m, 6H)

Example 32

10a-(4-(Benzyloxy)phenyl)-4-fluoro-6,7,8,9,10,10a-hexahydro-5aH-benzo[b]cyclohepta[d]furan (33)

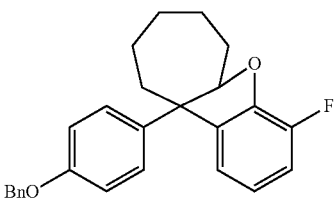

33

The title compound 33 was synthesized from alcohol 27 (75 mg) using procedure E described for the synthesis of 31. Yield: 51 mg (68%). $^1$H-NMR (400 MHz, CDCl$_3$): δ ppm 7.46-7.30 (m, 5H), 7.24-7.15 (m, 2H), 6.96 (ddd, J=10.69, 8.09, 1.23 Hz, 1H), 6.93-6.88 (m, 2H), 6.82 (dt, J=8.05, 7.96, 4.31 Hz, 1H), 6.74 (dd, J=7.51, 1.22 Hz, 1H), 5.05 (d, J=1.60 Hz, 1H), 5.03 (s, 2H), 2.39 (dd, J=14.35, 10.48 Hz, 1H), 2.26 (td, J=14.74, 7.38, 7.38 Hz, 1H), 2.12 (dd, J=14.62, 8.42 Hz, 1H), 1.94-1.84 (m, 1H), 1.82-1.04 (m, 6H).

Example 33

4-(6,7,8,9,10,10a-Hexahydro-5aH-benzo[b]cyclohepta[d]furan-10a-yl)phenol (807)

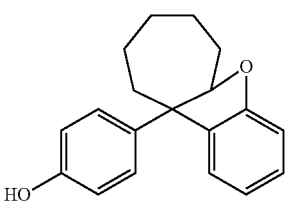

807

Procedure F

Pd on activated carbon (10%, 25 mg) was added to a solution of compound 31 in ethyl acetate (5 mL). A H$_2$ filled balloon was fitted. Stirred for 3 h at r.t., filtered through a plug of celite, concentrated and purified by flash chromatography (eluent: 100% dichloromethane). Yield: 34 mg, quantitatively. $^1$H-NMR (400 MHz, CDCl$_3$): δ ppm 7.20-7.13 (m, 3H), 6.99-6.95 (m, 1H), 6.92-6.84 (m, 2H), 6.77-6.72 (m, 2H), 4.93 (dd, J=2, 9 Hz, 1H), 4.84 (broad s, 1H), 2.42-2.34 (m, 1H), 2.24-2.06 (m, 2H), 1.92-1.84 (m, 1H), 1.78-1.28 (m, 6H).

Example 34

4-(2-Fluoro-6,7,8,9,10,10a-hexahydro-5aH-benzo[b]cyclohepta[d]-furan-10a-yl)phenol (448)

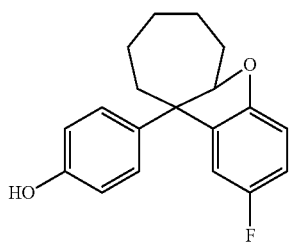

448

The title compound 448 was synthesized starting from compound 32 using the procedure F as described for the synthesis of phenol 807. $^1$H-NMR (400 MHz, CDCl$_3$): δ ppm 7.18-7.07 (m, 2H), 6.82 (dt, J=8.79, 8.79, 2.75 Hz, 1H), 6.78-6.69 (m, 3H), 6.62 (dd, J=8.20, 2.73 Hz, 1H), 5.08 (broad s, 1H), 4.91 (dd, J=7.30, 1.61 Hz, 1H), 2.45-2.26 (m, 1H), 2.23-1.95 (m, 2H), 1.82 (tdd, J=14.57, 12.67, 1.56, 1.56 Hz, 1H), 1.77-1.48 (m, 4H), 1.44-1.03 (m, 2H).

Example 35

4-(4-Fluoro-6,7,8,9,10,10a-hexahydro-5aH-benzo[b]cyclohepta-[d]furan-10a-yl)phenol (447)

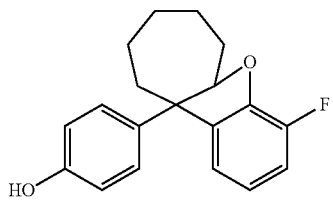

447

The title compound 447 was synthesized from compound 33 (51 mg) using procedure F described for the synthesis of phenol 807. Yield: 31 mg (77%). $^1$H-NMR (400 MHz, CDCl$_3$): δ ppm 7.14-7.07 (m, 2H), 6.93 (ddd, J=10.68, 8.09, 1.20 Hz, 1H), 6.78 (dt, J=8.02, 7.80, 4.33 Hz, 1H), 6.74-6.68 (m, 3H), 5.00 (dd, J=7.26, 1.60 Hz, 1H), 4.95 (s, 1H), 2.40-2.28 (m, 1H), 2.22 (td, J=14.78, 7.49, 7.49 Hz, 1H), 2.14-2.04 (m, 1H), 1.86 (tdd, J=14.64, 12.73, 1.56, 1.56 Hz, 1H), 1.78-1.49 (m, 4H), 1.16-0.96 (m, 1H), 1.43-1.29 (m, 1H)

Example 36

4-(1-Fluoro-5a,6,7,8,9,9a-hexahydrodibenzo[b,d]furan-9a-yl)phenol (130)

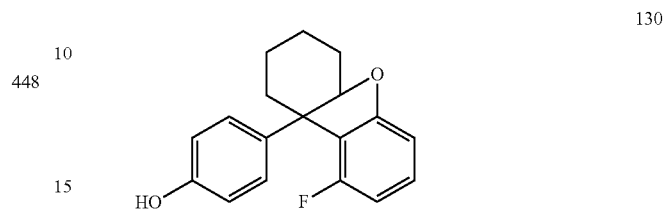

130

The title compound 130 was synthesized from alcohol 28 (10 mg) using the procedure E described for the synthesis of compound 31. LC MS/UV, m/z=285 (ESP+) was confirmed. Yield: 8 mg (79%). $^1$H-NMR (400 MHz, CDCl$_3$): δ ppm 7.29-7.20 (m, 2H), 7.16-7.08 (m, 1H), 6.81-6.75 (m, 2H), 6.63 (d, J=8 Hz, 1H), 6.54 (t, J=8 Hz, 1H), 4.83 (t, J=4 Hz, 1H), 4.70 (s, 1H), 2.38-2.28 (m, 1H), 2.17-2.08 (m, 1H), 1.98-1.89 (m, 1H), 1.87-1.73 (m, 1H), 1.72-1.60 (m, 2H), 1.55-1.46 (m, 2H):.

Example 37

9b-(4-(Benzyloxy)phenyl)-1,2,3,4,4a,9b-hexahydrodibenzo-[b,d]furan (34)

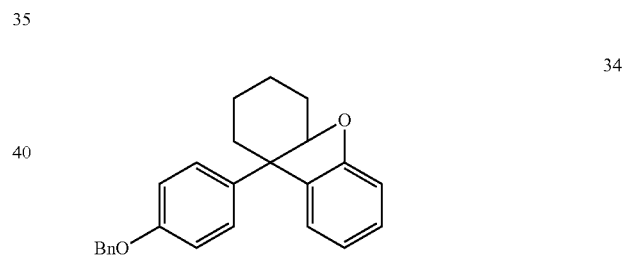

34

The title compound 34 was synthesized from alcohol 29 (60 mg) using procedure E described for the synthesis of compound 31. Yield: 50 mg (88%).

Example 38

4-(5a,6,7,8,9,9a-Hexahydrodibenzo[b,d]furan-9a-yl)phenol (961)

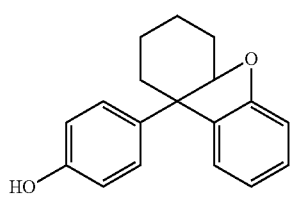

961

The title compound 961 was synthesized from compound 34 (10 mg) using the procedure described for the synthesis of compound 20. Purity LC MS/UV: m/z=265 (M−1) was confirmed. Yield: 7 mg (93%). $^1$H-NMR (400 MHz, CDCl$_3$): δ ppm 7.26-7.20 (m, 2H), 7.17-7.11 (m, 1H), 6.87-6.84 (m, 3H), 6.80-6.77 (m, 2H), 4.83 (t, J=4.29, 4.29 Hz, 1H), 4.67 (s, 1H), 2.35-2.22 (m, 1H), 2.05-1.96 (m, 1H), 1.86-1.50 (m, 6H).

Example 39

Experimental Description of Biochemical Assays

R-SAT® Assays

R-SAT® (Receptor Selection and Amplification Technology) is a cell-based functional assay that allows one to monitor receptor-dependent proliferative responses and has been described elsewhere. The technology has been validated for a number of receptors including GPCRs (Brauner-Osborne and Brann 1996), RTKs (Burstein et al. 1998), cytokine receptors (Piu et al. 2002) and nuclear receptors (Piu et al. 2005; Piu et al. 2006). This process is achieved by partial cellular transformation via loss of contact inhibition and growth factor dependency. Monitoring is achieved by transfecting the cells with a β-galactosidase reporter gene vector whose expression is under a constitutively active promoter. Briefly, NIH-3T3 fibroblasts were plated overnight in 96-wells plates in DMEM 10% calf serum (Hyclone) and grown to 60-70% confluency prior to transfection. Transient transfections were performed using Polyfect (Qiagen) according to manufacturer's instructions. Typically a transfection mix would consist of the receptor and the β-galactosidase expression vectors. Sixteen hours post-transfection, cells were incubated with different doses of ligand in DMEM containing 30% Ultraculture (Hyclone) and 0.4% calf serum (Hyclone) to generate a dose response curve. After 5 days, plates were developed by adding onto the washed cells a solution containing the β-galactosidase substrate o-nitrophenyl-D-galacto pyranoside ONPG (in phosphate-buffered saline with 5% Nonidet P-40 detergent) as described (Piu et al. 2002). Plates were read using a microplate reader at 420 nm. Data from R-SAT® assays were fit to the equation: r=A+B(x/(x+c)), where A=minimum response, B=maximum response minus minimum response, c=EC50, r=response, and x=concentration of ligand. Curves were generated using the curve fitting softwares Excel Fit and GraphPad Prism (San Diego, Calif.).

Luciferase Reporter Gene Assay

HEK293 cells were grown to 70% confluency in DMEM containing 10% calf serum (Hyclone) prior to transfection. On the day of transfection (day 1), expression vectors for ERa or ERb were cotransfected along a construct containing a synthetic 3*ERE (estrogen response element) upstream of the luciferase gene (Panomics), using Polyfect (Qiagen) per manufacturer's recommendations. Sixteen hours post-transfection, cells were incubated in serum free DMEM. On day 3, cells were incubated with the test compounds for 48 hours in serum free DMEM. Cells extracts were then obtained by lyzing and the Luciferase activity measured. All of these steps were performed using a commercially available kit (Promega).

Binding Assay

HEK293T cells were transiently transfected for 48 hours with expression vectors encoding ERα or ERβ, before being serum starved for 4-6 hours. Cells were then harvested by scraping in ice-cold PBS and subsequently lysed using a cold buffer containing 10 mM Tris pH 7.4, 1 mM EDTA, 1 mM DTT before being subjected to polytron twice for 10 seconds. Cytosolic extracts were isolated by centrifugation at 15000 g for 30 minutes at 4° C. Competitive binding of the test compounds or the estradiol control was performed on 20 uL extract by overnight incubation at 4° C. in a total volume of 100 μL containing 1 nM $^3$H-estradiol (Perkin Elmer, Boston, Mass.). The bound fraction was separated from the unbound one by the addition of 100 μL of Dextran coated charcoal, incubated for 10 minutes and subsequent centrifugation at 1000 rpm for 10 minutes. Samples (100 μL per sample) were then analyzed by liquid scintillation. Data was then analyzed using the curve fitting software GraphPad Prism.

Table Results for the Biochemical Assay and Microsomal Stability

| | R-SAT | | | | Luciferase | | | | Binding | |
|---|---|---|---|---|---|---|---|---|---|---|
| | ERα | | ERβ | | ERα | | ERβ | | ERα | ERβ |
| Comp # | % Eff | pEC$_{50}$ | % Eff | pEC$_{50}$ | % Eff | pEC$_{50}$ | % Eff | pEC$_{50}$ | pK$_i$ | pK$_i$ |
| 807 | 93 | 6.4 | 99 | 8.9 | 51 | 6.5 | 81 | 9.5 | 7.1 | 8.3 |
| 961 | 95 | 6.0 | 100 | 8.0 | 54 | 6.1 | 86 | 8.1 | | |
| 130 | 70 | 6.2 | 97 | 8.2 | 51 | 6.2 | 129 | 8.6 | 6.9 | 7.6 |
| 231 | 86 | 6.8 | 91 | 9.0 | 43 | 6.7 | 114 | 9.8 | | |
| 982 | 108 | 7.8 | 87 | 10.3 | | | | | | |
| 983 | na | na | na | na | | | | | | |
| 232 | 37 | 6.1 | 76 | 8.0 | 27 | 5.9 | 80 | 8.1 | | |
| 447 | 97 | 6.4 | 85 | 8.3 | 25 | 6.4 | 122 | 9.2 | | |
| 448 | 92 | 6.4 | 83 | 8.9 | 36 | 6.5 | 114 | 10.0 | | |
| 349 | 16 | | 24 | | 6.4 | 0 | | 6.5 | | | na = not active

What is claimed is:

1. A method of reducing inflammation, treating neuropathic pain, treating allergic conjunctivitis, treating dry eye, hormonal replacement therapy, lowering cholesterol, triglycerides, or LDL levels, treating impaired cognition or providing neuroprotection, preventing conception, treating colorectal cancer, prostate cancer, breast cancer, ovarian cancer, endometrial cancer, or uterine cancer or treating a disorder in a subject comprising:

identifying a subject in need thereof; and administering to the subject a pharmaceutically effective amount of one or more estrogen receptor β (ERβ) agonist;

wherein the disorder is selected from the group consisting of inflammatory bowel syndrome; Crohn's disease; ulcerative proctitis or colitis; prostatic hypertrophy; uterine leiomyomnas; breast carcinoma; endometrial carcinoma; polycystic ovary syndrome; endometrial polyps; benign breast disease; adenomyosis; ovarian carcinoma; melanoma; prostate carcinoma; colon carcinoma; brain tumors; prostatitis; interstitial cystitis; bone density loss; discholesterolemia; dislipidemia; cardiovascular disease; atherosclerosis; hypertension; peripheral vascular disease; restenosis; vasospasm; neurodegenerative disorders cognitive decline; stroke; anxiety; vaginal atrophy; vulvar atrophy; atrophic vaginitis; vaginal dryness; pruritus; dyspareunia; frequent urination; urinary incontinence; urinary tract infections; vasomotor symptoms; arthritis; psoriasis; dermatitis; asthma; pleurisy; multiple sclerosis; systemic lupus erthematosis; uveitis; sepsis; hemmorhagic shock; type II diabetes; acute or chronic inflammation; acute or chronic pain; lung disorders; ophthalmologic disorders; and free radical induced disease states; and wherein the ERβ agonist is a compound of Formula I:

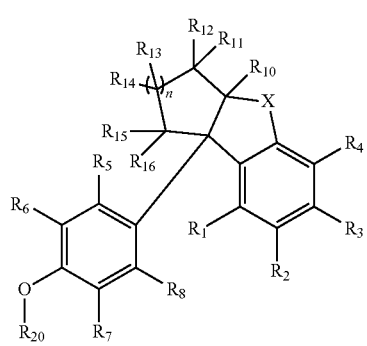

(I)

or a pharmaceutically acceptable salt or metabolite thereof, wherein:

X is selected from the group consisting of oxygen, sulfur, S=O, and SO$_2$;

n is an integer selected from the group consisting of 1, 2, 3 and 4;

$R_{20}$ is selected from the group consisting of hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heteroalicyclyl, haloalkyl, perhaloalkyl, sulphonyl, —C(=Z)R$_{30}$, —C(=Z)OR$_{30}$, —C(=Z)NR$_{31}$R$_{32}$, —S(O)NR$_{31}$R$_{32}$, —S(O)$_2$NR$_{31}$R$_{32}$, —P(=O)(OR$_{30}$), and —CH$_2$O(C=O)R$_{30}$;

$R_1$, $R_2$, $R_3$, and $R_4$ are each separately and independently selected from the group consisting of hydrogen, C$_{1-6}$alkyl, C$_{2-6}$alkenyl, C$_{2-6}$alkynyl, C$_{3-6}$cycloalkyl, C$_{1-6}$alkyl(C$_{3-6}$cycloalkyl), halogen, C$_{1-6}$haloalkyl, C$_{1-6}$perhaloalkyl, C$_{1-6}$haloalkoxy, —CN, —C(=Z)R$_{30}$, —C(=Z)OR$_{30}$, —C(=Z)NR$_{31}$R$_{32}$, —C(R$_{30}$)=NR$_{31}$, —NR$_{31}$R$_{32}$, —N=CR$_{31}$R$_{32}$, —N(R$_{30}$)—C(=Z)R$_{30}$, —N(R$_{30}$)—C(=Z)NR$_{31}$R$_{32}$, —S(O)NR$_{31}$R$_{32}$, —S(O)$_2$NR$_{31}$R$_{32}$, —N(R$_{30}$)—S(=O)R$_{30}$, —N(R$_{30}$)—S(=O)$_2$R$_{30}$, —OR$_{30}$, —SR$_{30}$, and —OC(=Z)R$_{30}$; wherein said alkyl, alkenyl, alkynyl, cycloalkyl and alkoxy are optionally substituted;

or two of $R_1$, $R_2$, $R_3$, and $R_4$ on adjacent carbons taken together, along with the two intervening carbons to which they are attached, form a C$_{3-6}$cycloalkenyl, aryl, heteroaryl or C$_{3-6}$heterocycloalkenyl group;

$R_5$, $R_6$, $R_7$, and $R_8$ are each separately and independently selected from the group consisting of hydrogen, C$_{1-6}$alkyl, C$_{2-6}$alkenyl, C$_{2-6}$alkynyl, C$_{3-6}$cycloalkyl, C$_{1-6}$alkyl(C$_{3-6}$cycloalkyl), halogen, C$_{1-6}$haloalkyl, C$_{1-6}$perhaloalkyl, C$_{1-6}$haloalkoxy, —CN, —C(=Z)R$_{30}$, —C(=Z)OR$_{30}$, —C(=Z)NR$_{31}$R$_{32}$, —C(R$_{30}$)=NR$_{31}$, —NR$_{31}$R$_{32}$, —N=CR$_{31}$R$_{32}$, —N(R$_{30}$)—C(=Z)R$_{30}$, —N(R$_{30}$)—C(=Z)NR$_{31}$R$_{32}$, —S(O)NR$_{31}$R$_{32}$, —S(O)$_2$NR$_{31}$R$_{32}$, —N(R$_{30}$)—S(=O)R$_{30}$, —N(R$_{30}$)—S(=O)$_2$R$_{30}$, —OR$_{30}$, —SR$_{30}$, and —OC(=Z)R$_{30}$; wherein said alkyl, alkenyl, alkynyl, cycloalkyl and alkoxy are optionally substituted;

or two of $R_5$, $R_6$, $R_7$, and $R_8$ on adjacent carbons taken together, along with the two intervening carbons to which they are attached, form a C$_{3-6}$cycloalkenyl, aryl, heteroaryl or C$_{3-6}$heterocycloalkenyl group;

$R_{10}$, $R_{11}$, $R_{12}$, $R_{13}$, $R_{14}$, $R_{15}$, and $R_{16}$ are each separately and independently selected from the group consisting of hydrogen, C$_{1-6}$alkyl, C$_{2-6}$alkenyl, C$_{2-6}$alkynyl, C$_{3-6}$cycloalkyl, C$_{1-6}$alkyl(C$_{3-6}$cycloalkyl), halogen, C$_{1-6}$haloalkyl, C$_{1-6}$perhaloalkyl, C$_{1-6}$haloalkoxy, —CN, —C(=Z)R$_{30}$, —C(=Z)OR$_{30}$, —C(=Z)NR$_{31}$R$_{32}$, —C(R$_{30}$)=NR$_{31}$, —NR$_{31}$R$_{32}$, —N=CR$_{31}$R$_{32}$, —N(R$_{30}$)—C(=Z)R$_{30}$, —N(R$_{30}$)—C(=Z)NR$_{31}$R$_{32}$, —S(O)NR$_{31}$R$_{32}$, —S(O)$_2$NR$_{31}$R$_{32}$, —N(R$_{30}$)—S(=O)R$_{30}$, —N(R$_{30}$)—S(=O)$_2$R$_{30}$, —OR$_{30}$, —SR$_{30}$, and —OC(=Z)R$_{30}$; wherein said alkyl, alkenyl, alkynyl, cykloalkyl and alkoxy is optionally substituted;

or two geminal $R_{11}$, $R_{12}$, $R_{13}$, $R_{14}$, $R_{15}$, and $R_{16}$ taken together, along with the carbon atom to which they are attached, form a carbonyl group;

or two geminal $R_{11}$, $R_{12}$, $R_{13}$, $R_{14}$, $R_{15}$, and $R_{16}$ taken together, along with the carbon atom to which they are attached, form a C$_{3-6}$cycloalkyl or C$_{2-6}$heterocycloalkyl group;

or two geminal $R_{11}$, $R_{12}$, $R_{13}$, $R_{14}$, $R_{15}$, and $R_{16}$ taken together, along with the carbon atom to which they are attached, form a C$_{2-6}$alkylidene group;

or two $R_{10}$, $R_{11}$, $R_{12}$, $R_{13}$, $R_{14}$, $R_{15}$, and $R_{16}$ on adjacent carbons, taken together along with the two intervening carbon atoms to which they are attached, form a double bond;

or one of $R_{10}$, $R_{11}$, $R_{12}$, $R_{13}$, $R_{14}$, $R_{15}$, and $R_{16}$ and the carbon atom to which it is attached and the carbon atom to which one adjacent $R_{10}$, $R_{11}$, $R_{12}$, $R_{13}$, $R_{14}$, $R_{15}$, and $R_{16}$ is attached, form a C$_{3-6}$cycloalkyl or C$_{2-6}$heterocycloalkyl group, provided that one or more of $R_{10}$-$R_{16}$ is not present to complete the octet of all carbon atoms;

or one of $R_{10}$, $R_{11}$, $R_{12}$, $R_{13}$, $R_{14}$, $R_{15}$, and $R_{16}$ and the carbon atom to which it is attached and the carbon atom to which one non-adjacent $R_{10}$, $R_{11}$, $R_{12}$, $R_{13}$, $R_{14}$, $R_{15}$, and $R_{16}$ is attached, taken together with all intervening carbon atoms, form a C$_{3-6}$cycloalkyl or C$_{2-6}$heterocycloalkyl group, provided that one or more of $R_{10}$-$R_{16}$ is not present to complete the octet of all carbon atoms;

or one of $R_5$, $R_6$, $R_7$, and $R_8$ and the carbon atom to which it is attached and the carbon atom to which one of $R_{10}$, $R_{11}$, $R_{12}$, $R_{13}$, $R_{14}$, $R_{15}$, and $R_{16}$ is attached and at least two intervening carbon atoms, or one of $R_{10}$, $R_{11}$, $R_{12}$, $R_{13}$, $R_{14}$, $R_{15}$, and $R_{16}$ and the carbon atom to which it is attached and the carbon atom to which one of $R_5$, $R_6$, $R_7$, and $R_8$ is attached and at least two intervening carbon atoms, form a C$_{5-7}$cycloalkenyl or C$_{4-7}$heterocycloalkyl group, provided that one or more of $R_5$-$R_{16}$ is not present to complete the octet of all carbon atoms;

Z is oxygen or sulfur; and $R_{30}$, $R_{31}$ and $R_{32}$ are each independently selected from the group consisting of hydrogen, optionally substituted $C_{1-6}$alkyl, optionally substituted $C_{2-6}$alkenyl, optionally substituted $C_{2-6}$alkynyl, optionally substituted $C_{3-6}$cycloalkyl, optionally substituted $C_{3-6}$cycloalkenyl, optionally substituted aryl, optionally substituted heteroaryl, optionally substituted $C_{2-6}$heteroalicyclyl;

or $R_{31}$ and $R_{32}$ taken together, along with the nitrogen atom to which they are attached, form a heterocycloalkyl group;

or $R_{31}$ and $R_{32}$ taken together, along with the carbon atom to which they are attached, form a $C_{3-6}$cycloalkyl or heterocycloalkyl group.

2. The method of claim 1, wherein the inflammation is in the eye, in the gastrointestinal tract, results in lid edema, hyperemia, chemosis, or tearing, or is due to arthritis, an ophthalmologic disorder selected from the group consisting of uveitis, blepharitis, meibonian gland disease, glaucoma, dry eye, or macular degeneration, or is an ocular manifestation of a systemic inflammatory disease selected from Sjogrens Syndrome, ocular sicatricial pemphygoid and Lupus erythmatosis.

3. The method of claim 1, wherein the inflammation is acute or chronic inflammation and the neuropathic pain is associated with a medical condition selected from the group of traumatic nerve injury, multiple sclerosis, stroke, syringomyelia, epilepsy, spinal cord injury, and cancer.

4. The method of claim 1, wherein the neuropathic pain is selected from the group of hyperalgesia, tactile hyperalgesia, allodynia phantom limb pain, postherpetic neuralgia, reflex sympathetic dystrophy, causalgia, complex regional pain syndrome II, painful HIV-associated neuropathy, and diabetic neuropathy.

5. The method of claim 1, wherein the optionally substituted substituents for $R_1$-$R_{16}$ are each independently substituted with a substituent selected from the group consisting of —CN, halogen, haloalkyl, —O($C_{1-6}$alkyl), —N$R_{31}R_{32}$, —S($C_{1-6}$alkyl), —O($C_{1-6}$haloalkyl).

6. The method of claim 1, wherein X is oxygen or sulfur.

7. The method of claim 1, wherein $R_1$, $R_2$, $R_3$, and $R_4$ are each separately and independently selected from the group consisting of hydrogen, optionally substituted $C_{1-6}$alkyl, optionally substituted $C_{3-6}$cycloalkyl, optionally substituted $C_{1-6}$alkyl($C_{3-6}$cycloalkyl), halogen, optionally substituted $C_{1-6}$haloalkyl, optionally substituted $C_{1-6}$haloalkoxy, —CN, —C(=Z)$R_{30}$, —C(=Z)O$R_{30}$, —C(=Z)N$R_{31}R_{32}$, —C($R_{30}$)=N$R_{31}$, —N$R_{31}R_{32}$, and —N=C$R_{31}R_{32}$.

8. The method of claim 1, wherein $R_1$, $R_2$, $R_3$, and $R_4$ are each selected from the group consisting of hydrogen, fluoro, and chloro.

9. The method of claim 1, wherein $R_5$, $R_6$, $R_7$, and $R_8$ are each separately and independently selected from the group consisting of hydrogen, optionally substituted $C_{1-6}$alkyl, optionally substituted $C_{3-6}$cycloalkyl, optionally substituted $C_{1-6}$alkyl($C_{3-6}$cycloalkyl), halogen, optionally substituted $C_{1-6}$haloalkyl, optionally substituted $C_{1-6}$haloalkoxy, —CN, —C(=Z)$R_{30}$, —C(=Z)O$R_{30}$, —C(=Z)N$R_{31}R_{32}$, —C($R_{30}$)=N$R_{31}$, —N$R_{31}R_{32}$, and —N=C$R_{31}R_{32}$.

10. The method of claim 1, wherein $R_5$, $R_6$, $R_7$, and $R_8$ are each selected from the group consisting of hydrogen and fluoro.

11. The method of claim 1, wherein $R_{10}$, $R_{11}$, $R_{12}$, $R_{13}$, $R_{14}$, $R_{15}$, and $R_{16}$ are each separately and independently selected from the group consisting of hydrogen, optionally substituted $C_{1-6}$alkyl, optionally substituted $C_{3-6}$cycloalkyl, optionally substituted $C_{1-6}$alkyl($C_{3-6}$cycloalkyl), halogen, optionally substituted $C_{1-6}$haloalkyl, optionally substituted $C_{1-6}$haloalkoxy, —CN, —C(=Z)$R_{30}$, —C(=Z)O$R_{30}$, —C(=Z)N$R_{31}R_{32}$, —C($R_{30}$)=N$R_{31}$, —N$R_{31}R_{32}$, and —N=C$R_{31}R_{32}$.

12. The compound of claim 1, wherein $R_{10}$, $R_{11}$, $R_{12}$, $R_{13}$, $R_{14}$, $R_{15}$, and $R_{16}$ are each selected from the group consisting of hydrogen and fluoro.

13. The method of claim 1, wherein two of $R_{10}$, $R_{11}$, $R_{12}$, $R_{13}$, $R_{14}$, $R_{15}$, and $R_{16}$ on adjacent carbons taken together, along with the two intervening carbon atoms to which they are attached, form a double bond.

14. The method of claim 1, wherein $R_{20}$ is selected from the group consisting of hydrogen, optionally substituted alkyl, optionally substituted cycloalkyl, optionally substituted aryl, optionally substituted heteroaryl, optionally substituted heteroalicyclyl, and haloalkyl.

15. The method of claim 1, wherein $R_{20}$ is selected from the group consisting of hydrogen and methyl.

16. The method of claim 1, wherein n is 2 or 3.

17. The method of claim 1, wherein the compound is selected from the group consisting of

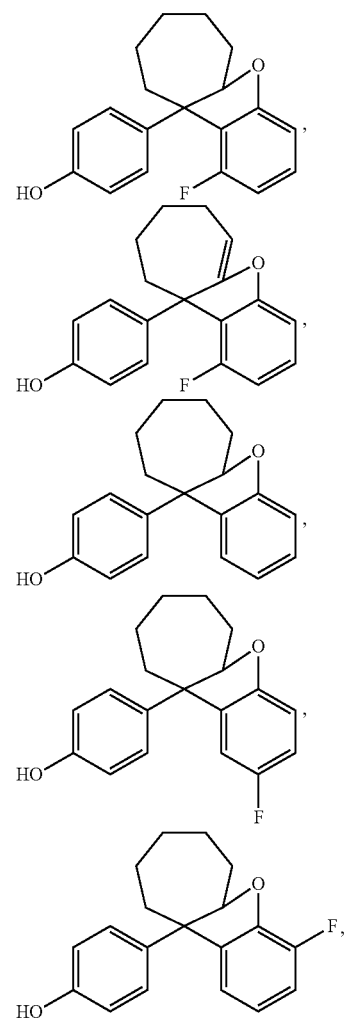

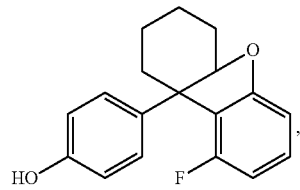
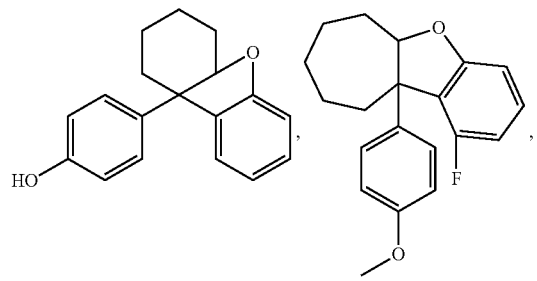
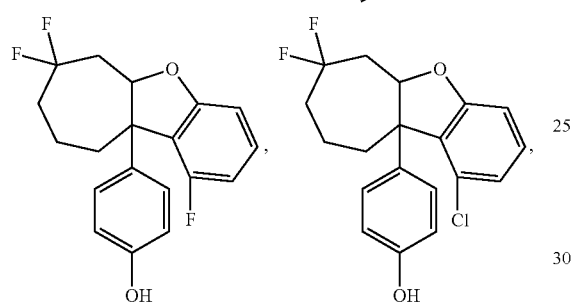
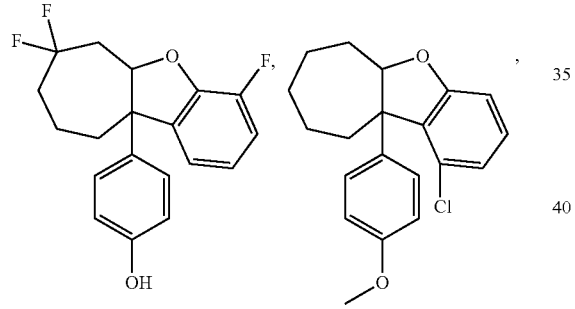
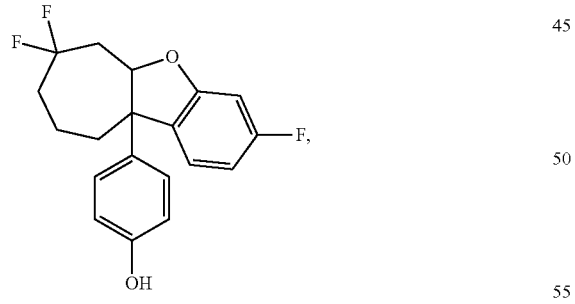
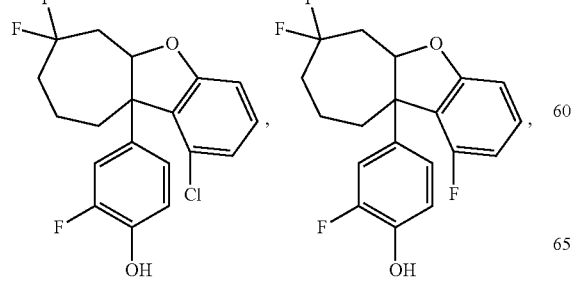
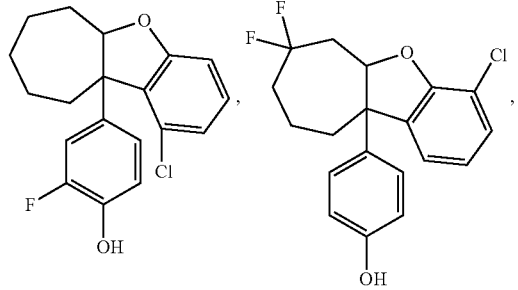
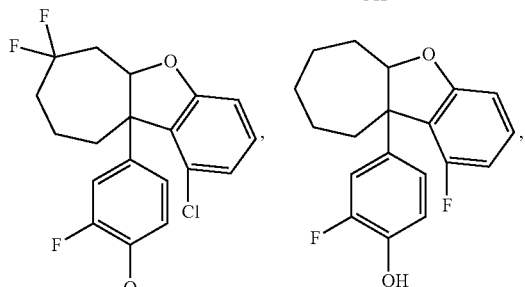
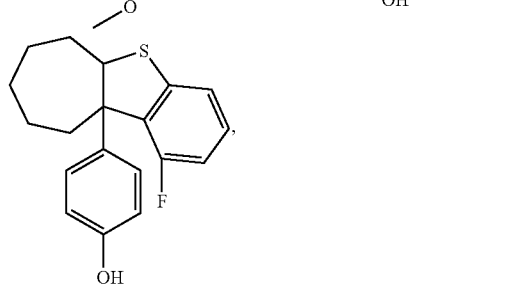
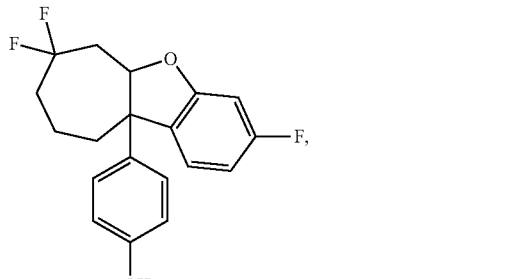
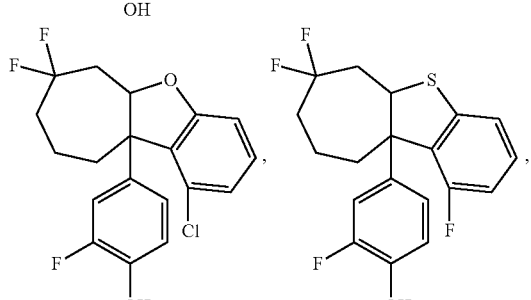
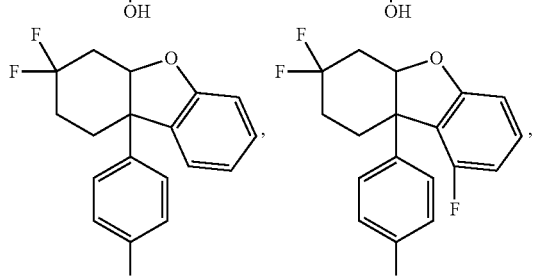

-continued
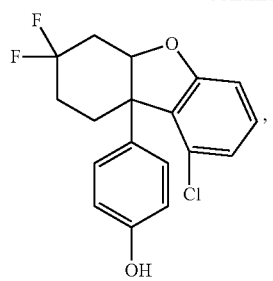
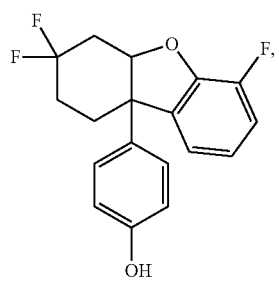
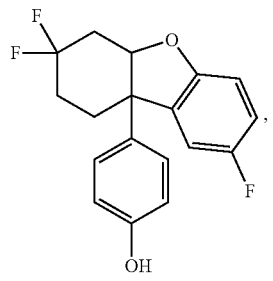
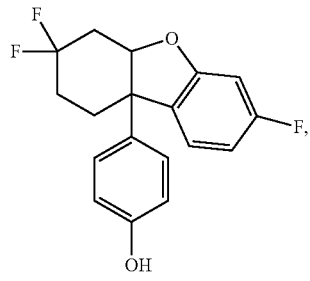
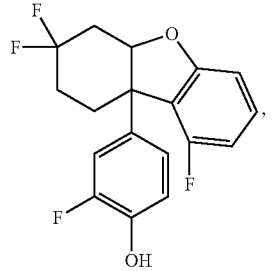 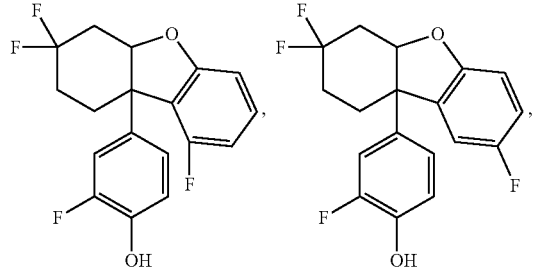
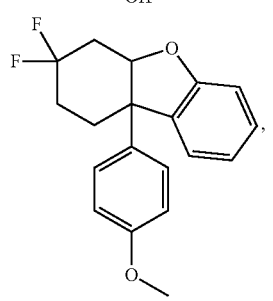 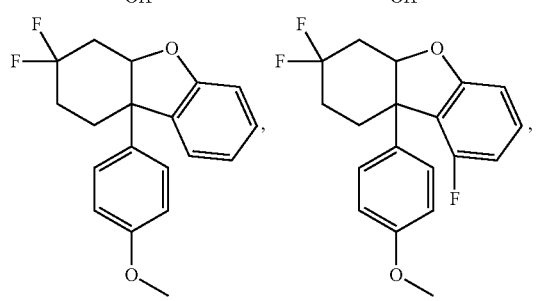
-continued
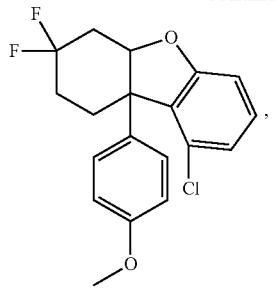
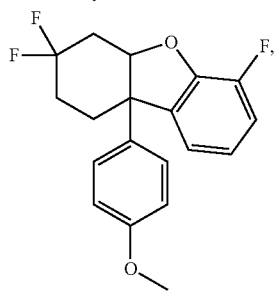
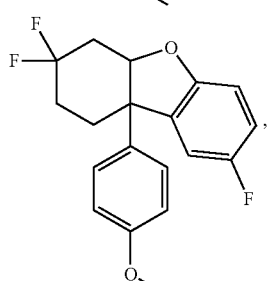
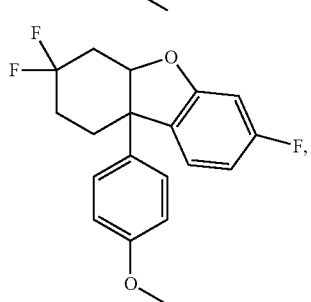
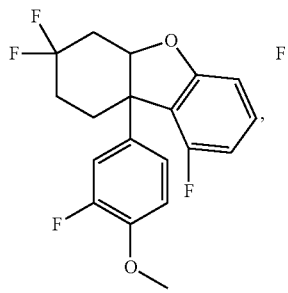
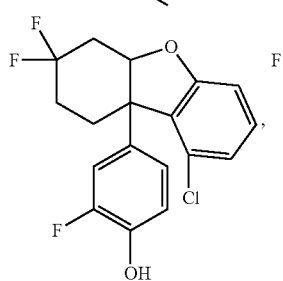

-continued

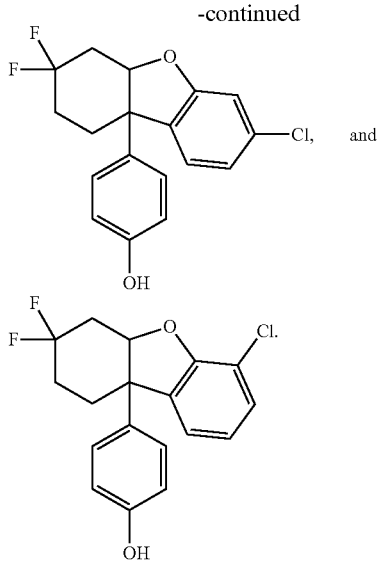

18. The method of claim 1, wherein the disorder is selected from the group consisting of Alzheimer's disease, Huntington's disease, and Parkinson's disease.

19. The method of claim 1, wherein the disorder is Alzheimer's disease or Parkinson's disease.

20. The method of claim 1, wherein the brain tumor is selected from glioblastoma, astrocytoma, glioma, and meningioma.

21. The method of claim 1, wherein the bone density loss is selected from osteoporosis and osteopenia.

22. The method of claim 1, wherein the neurodegenerative disorder is selected from Alzheimer's disease, Huntington's disease, Parkinson's disease, and other dementias.

23. The method of claim 1, wherein the vasomotor symptom is selected from flusing and hot flashes.

24. The method of claim 1, wherein the arthritis is selected from rheumatoid arthritis, osteoarthritis, and arthropathiesendometriosis.

25. The method of claim 1, wherein the lung disorder is selected from asthma and chronic obstructive pulmonary disease.

26. The method of claim 1, wherein the ophthalmologic disorder is selected from glaucoma, dry eye, and macular degeneration.

* * * * *